(12) United States Patent
Tredwell et al.

(10) Patent No.: US 9,348,034 B2
(45) Date of Patent: May 24, 2016

(54) INDIRECT RADIOGRAPHIC IMAGING SYSTEMS INCLUDING INTEGRATED BEAM DETECT

(71) Applicant: Carestream Health, Inc., Rochester, NY (US)

(72) Inventors: Timothy J. Tredwell, Fairport, NY (US); Victor C. Wong, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 14/423,441

(22) PCT Filed: Sep. 6, 2013

(86) PCT No.: PCT/US2013/058408
§ 371 (c)(1),
(2) Date: Feb. 24, 2015

(87) PCT Pub. No.: WO2014/039765
PCT Pub. Date: Mar. 13, 2014

(65) Prior Publication Data
US 2015/0185334 A1    Jul. 2, 2015

Related U.S. Application Data

(60) Provisional application No. 61/698,573, filed on Sep. 8, 2012.

(51) Int. Cl.
*G01T 1/20* (2006.01)
*A61B 6/12* (2006.01)
*G01T 1/161* (2006.01)
*A61B 6/00* (2006.01)

(52) U.S. Cl.
CPC ... *G01T 1/20* (2013.01); *A61B 6/12* (2013.01); *G01T 1/161* (2013.01); *A61B 6/4233* (2013.01); *A61B 6/542* (2013.01)

(58) Field of Classification Search
CPC ............ G01T 1/20; G01T 1/023; A61B 6/12
See application file for complete search history.

(56) References Cited

U.S. PATENT DOCUMENTS 9,104,097 B2 * 8/2015 Suwa .................... G03B 42/04
2002/0070365 A1 * 6/2002 Karellas ............... A61B 6/4258
250/581

(Continued)

FOREIGN PATENT DOCUMENTS

JP    2010-127630    6/2010

OTHER PUBLICATIONS

International Search Report mailed Dec. 16, 2013 for International Application No. PCT/US2013/058408, 3 pages.

*Primary Examiner* — David Porta
*Assistant Examiner* — Faye Boosalis

(57) ABSTRACT

A wireless X-ray detector for a digital radiography system with remote detection of impinging radiation from the system X-ray source onto a sensor panel having amorphous or crystalline silicon photodiodes or metal insulated semiconductor (MIS) sensors. Certain exemplary embodiments described herein can provide a digital radiography detector including a housing having first and second spaced members and side walls defining a cavity; a radiographic image detector assembly mounted within the cavity for converting a radiographic image to an electronic radiographic image, wherein the detector assembly includes a scintillator screen and a detector imaging array; and a light guiding element positioned proximate the radiographic image detector assembly to detect a start of exposure, a termination of the exposure, dose for the exposure or rate of dose for the exposure using light generated by the scintillator screen.

18 Claims, 23 Drawing Sheets

(56) References Cited

U.S. PATENT DOCUMENTS

| | | |
|---|---|---|
| 2007/0112596 A1 | 5/2007 | Exelmans |
| 2007/0181815 A1 | 8/2007 | Ebstein |
| 2009/0146070 A1 | 6/2009 | Vieira Da Rocha et al. |
| 2011/0095442 A1 | 4/2011 | Greener et al. |
| 2011/0133093 A1 | 6/2011 | Jagannathan et al. |

* cited by examiner

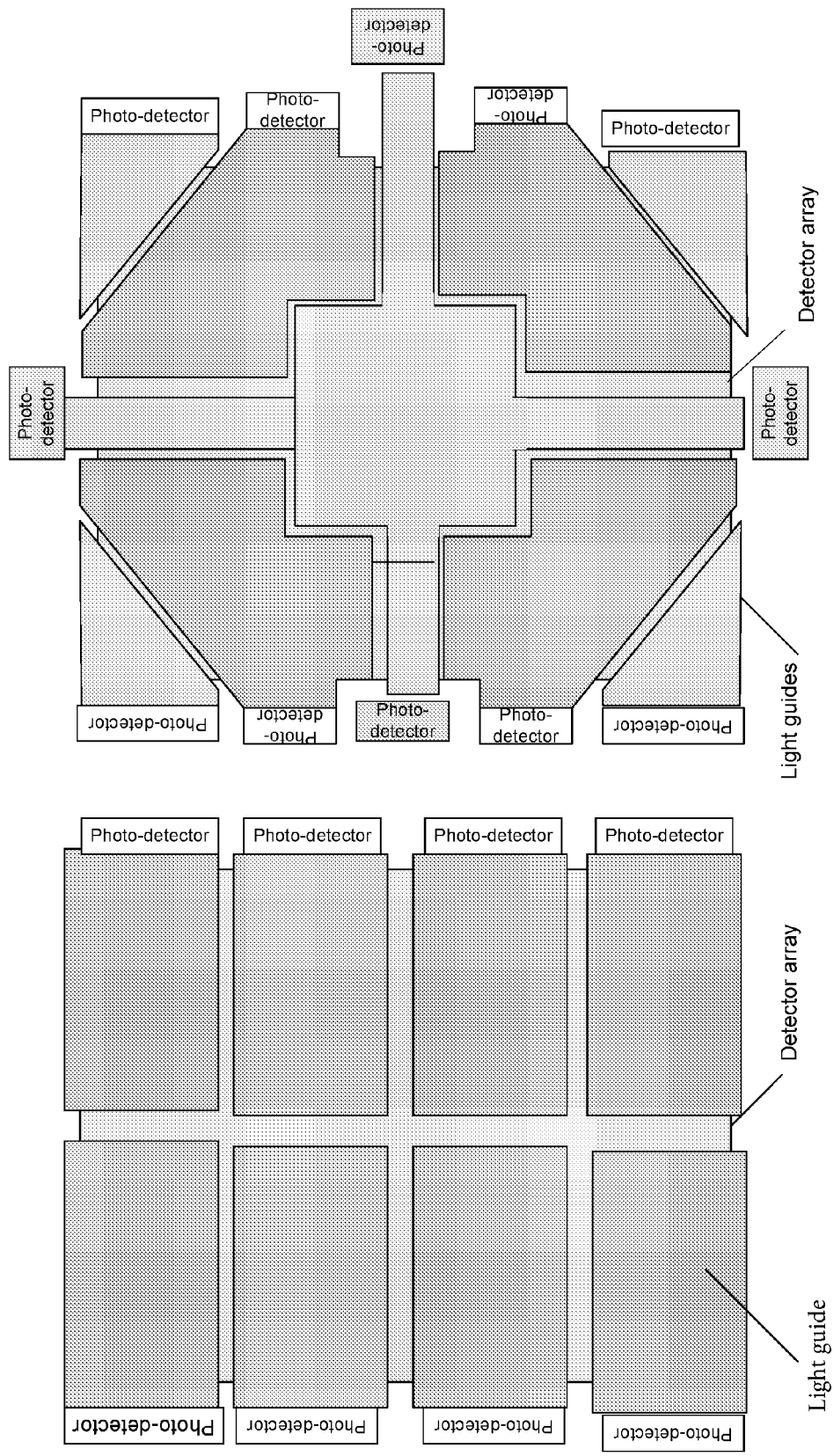
FIG. 14 Separate light guides positioned over various portions of the detector array to provide individual monitoring of X-ray exposure in various regions of the detector

INDIRECT RADIOGRAPHIC IMAGING SYSTEMS INCLUDING INTEGRATED BEAM DETECT

FIELD OF THE INVENTION

The invention relates generally to the field of medical imaging, and in particular to digital radiography. More specifically, the invention relates to a wireless X-ray detector for a digital radiography system employing remote X-ray event detection.

BACKGROUND OF THE INVENTION

There exists a need for a wireless X-ray imaging sensor panel of the type using amorphous or crystalline silicon photodiodes or metal insulated semiconductor (MIS) sensors that is capable of operating independently of the main imaging system and that can remotely and reliably detect both the onset and cessation of impinging X-rays from an X-ray source in the main imaging system.

SUMMARY

An aspect of this application is to advance the art of medical digital radiography.

Another aspect of this application is to address, in whole or in part, at least the foregoing and other deficiencies in the related art.

It is another aspect of this application to provide, in whole or in part, at least the advantages described herein.

An aspect of this application is to provide methods and/or apparatus to address and/or reduce disadvantages caused by the noninvasive x-ray beam detection for portable wireless digital radiography detectors.

This application relates to scintillating screens, digital X-ray detectors (DXD) and digital X-ray capture systems. Exemplary embodiments can provide methods and/or apparatus by which one or more of (a) the start of exposure, (b) the intensity of exposure (c) the end of exposure and (d) the total dose, and (e) dose and/or dose rate vs. x-y position on the detector may be detected independent of the imaging array to which the scintillating screen is attached.

In accordance with one embodiment, the present invention can provide a digital radiography detector that can include a housing having first and second spaced planar members and side walls defining a cavity; a radiographic image detector assembly mounted within the cavity for converting a radiographic image to an electronic radiographic image, wherein the detector assembly includes a scintillator screen and a detector imaging array; and a light guiding element positioned proximate the radiographic image detector assembly to redirect light for detection of a start of exposure, a termination of the exposure, dose for the exposure or rate of dose for the exposure using light generated by the scintillator screen.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

FIG. 14 is a diagram that shows a plurality of independent light guides positioned corresponding to (e.g., over) various portions of a radiographic detector array to provide individual monitoring of X-ray exposure in various regions of the detector v according to the application.

DESCRIPTION OF EXEMPLARY EMBODIMENTS

The following is a description of exemplary embodiments of the invention, examples of which are illustrated in the accompanying drawings. Wherever possible, the same reference numbers will be used throughout the drawings to refer to the same or like parts.

For illustrative purposes, principles of the invention are described herein by referring mainly to exemplary embodiments thereof. However, one of ordinary skill in the art would readily recognize that the same principles are equally applicable to, and can be implemented in, all types of radiographic imaging arrays, various types of radiographic imaging apparatus and/or methods for using the same and that any such variations do not depart from the true spirit and scope of the application. Moreover, in the following description, references are made to the accompanying figures, which illustrate specific exemplary embodiments. Electrical, mechanical, logical and structural changes can be made to the embodiments without departing from the spirit and scope of the invention.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. Where they are used, the terms "first", "second", and so on, do not necessarily denote any ordinal or priority relation, but may be used for more clearly distinguishing one element or time interval from another.

Figure 1:
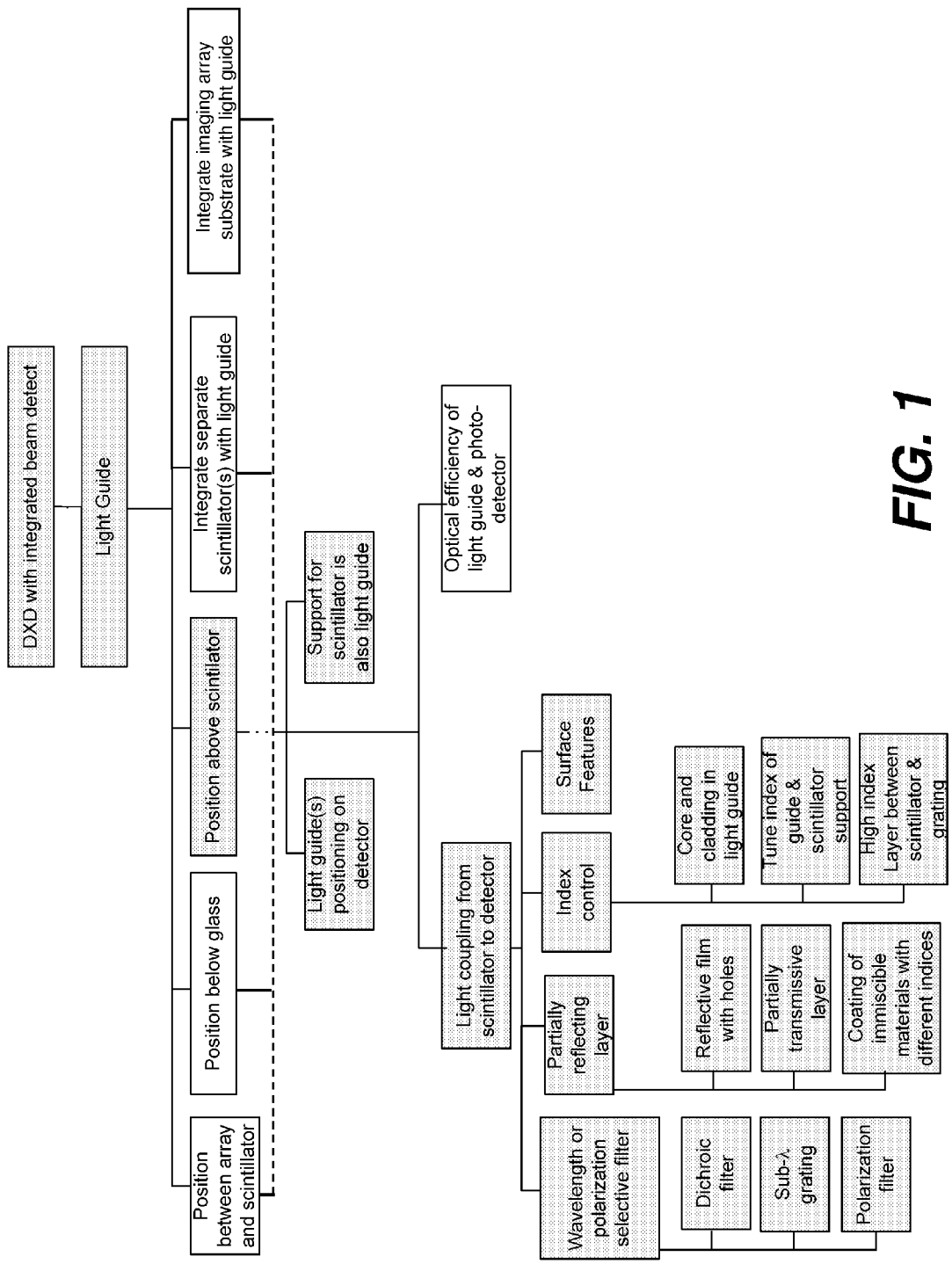
FIG. 1 is a diagram that shows a chart of features of radiographic imaging systems including exemplary integrated beam detect including a light transfer unit according to the application.

Exemplary embodiments for DXD with integrated beam detect are shown in FIG. 1. As shown by the dotted lines in FIG. 1, exemplary embodiments of light guiding elements can be variously positioned and/or integrated within a radiographic imaging system, which can be used for a digital radiographic detector 100. As shown in FIG. 1, various embodiments for a light transfer and photosensor units according to the application can be operatively positioned adjacent, nearby, within or as part of a support or substrate for an imaging array. Further, light guiding element embodiments can include a light guide element positioned in a digital radiographic detector below a substrate for an imaging array, between the substrate for and the imaging array, between an imaging array and a scintillator, above a scintillator, integrated within the scintillator (e.g., at the scintillator support) and/or integrated within the substrate for the imaging array. Additionally, various light guiding element embodiments will be described functionally with respect to exemplary implementations using a scintillator screen with respect to FIGS. 2-13, however, embodiments according to the application are not intended to be so limited as such functional interactions of light guiding element embodiments can be implemented at least at the various positions described within a digital radiographic detector shown in FIG. 1. Again, exemplary light guiding element embodiments can provide methods and/or apparatus by which one or more of (a) the start of exposure, (b) the intensity of exposure (c) the end of exposure and (d) the total dose, and (e) dose and/or dose rate vs. x-y position on the radiographic detector may be detected independent of the imaging array to which the scintillating screen is attached. Thus, exemplary light guiding element embodiments can provide methods and/or apparatus by which integrated beam detection functionality is provided to a radiographic detector.

Figure 2:
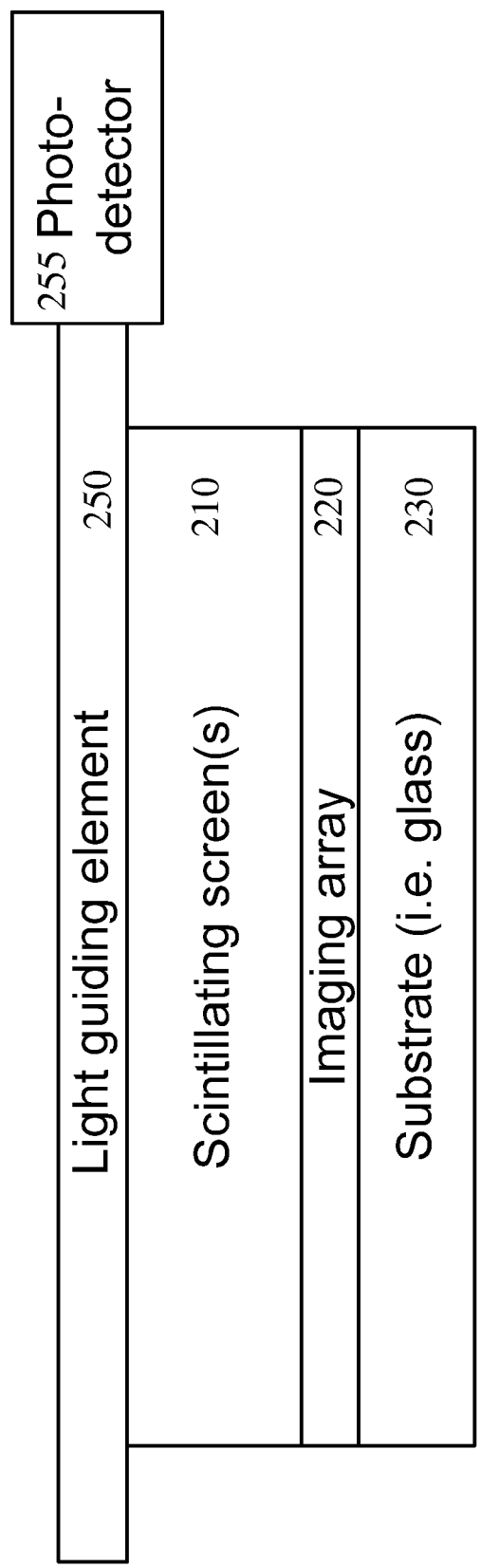
FIG. 2 is a diagram that shows an embodiment of a light detection apparatus mounted near a scintillator in a digital radiographic detector according to the application.

Certain exemplary embodiments according to the application relate to systems and/or methods in which a light guiding element is positioned proximate the scintillator screen and/or radiographic imaging array, for example, positioned on a side of the scintillating screen opposite the side of the screen proximate the imaging array (e.g., see FIG. 2).

For certain exemplary embodiments, the scintillating screen can be provided with a light collection film, which can extract a portion of the light from the scintillator and guide that light to a spaced apart light detection element (e.g., on the perimeter of the screen). Light guiding films are well known in the display industry, where they are used in edge-illuminated LCD panels. When lit from the side using an optical coupling element, the light from the LED's can be inserted into the optical film or plate. The light is totally internally reflected in the light guiding element unless it encounters an optical discontinuity that can cause the light to travel at an angle to the plate surface that defeats total internal reflection. Patterned topography in the film surface can cause a portion of the light to be scattered out of the film and into the LCD pixel elements. In display applications, a diffusing film is often inserted between the light guiding film and the LCD array in order to uniformize light emission spatially. These films are thin (0.5 mm to 2 mm thick), large area, and usually fabricated from plastics (such as PMMA, acrylics or other transparent plastics, (See, for example, US20110095442). Optical plates formed from glass or air-guides may also be used. The light guiding film may also contain a photo-detector to monitor the illumination level inside the film as feedback to the LED sources. The placement of the patterned topography can be uniform across the backlight or it may be spatially non-uniform in order to compensate for light loss as the light travels across the film. These films are highly efficient, with a percentage of the light from the LED coupled into the LCD pixel elements.

FIG. 2 is a diagram that shows an embodiment of a light detection apparatus mounted near a scintillator in a digital radiographic detector according to the application. As shown in FIG. 2, a scintillating screen 210 can be arranged in proximity to a light detection (e.g., radiographic imaging) array 220. The scintillator screen 210 may deposited directly onto the imaging array 220, which can be over a substrate 230. Alternatively, the scintillator screen 210 may be laminated or attached adhesively to the imaging array 220, or held in contact with the imaging array 220. One or more light-guiding elements 250 can be attached to the scintillator screen 210 opposite the imaging array 220. The light-guiding elements 250 can transmit a portion of the light emitted from the scintillator screen 210 and guide at least a portion of the transmitted light to one or more light-detection elements 255 (e.g. a photodetector), for example, arranged peripheral to the imaging array 220. In one embodiment, the light-guiding elements 250 and/or the light-detection element 255 are outside (e.g., not contained in or over) of an imaging area of the imaging array or detector.

Figure 3:
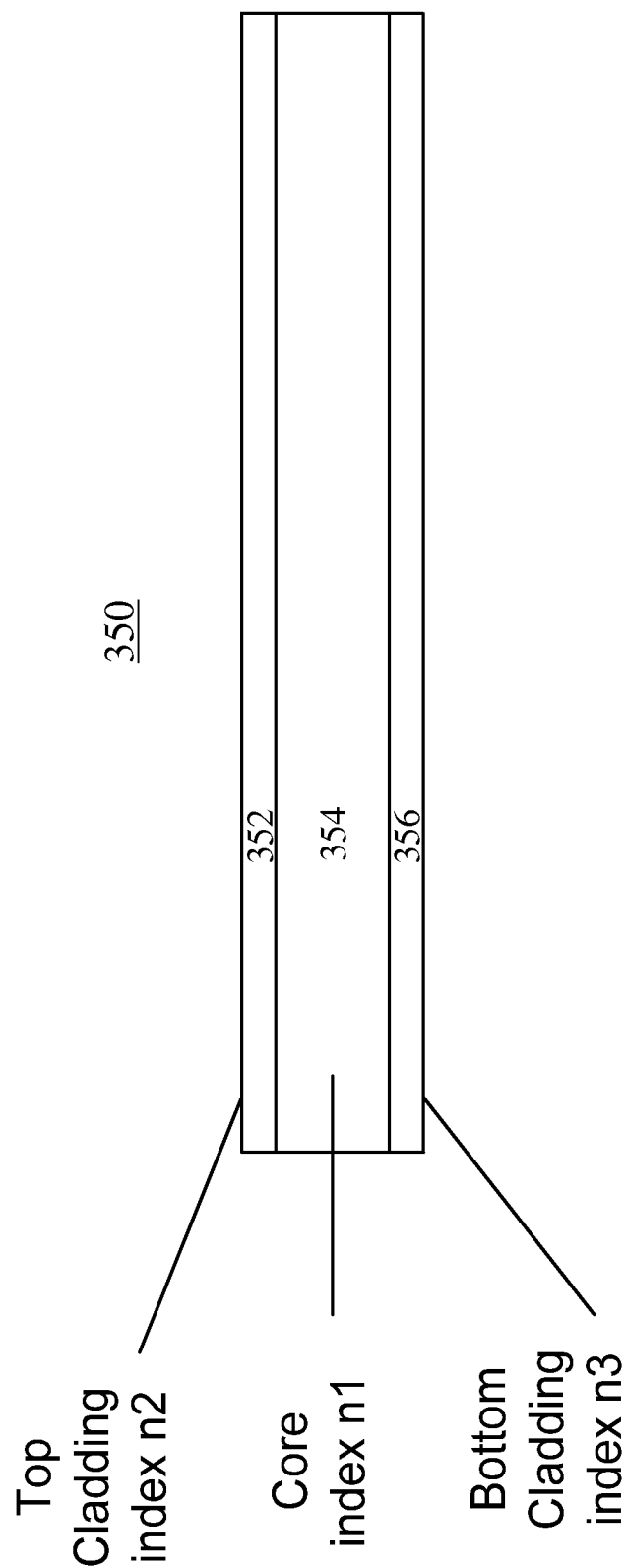
FIG. 3 is a diagram that shows exemplary integrated beam detect including a light transfer unit embodiment positioned proximate a scintillator of radiographic imaging systems according to the application.

In one embodiment, a light guiding element may be a single sheet or plate of optically transparent material. FIG. 3 is a diagram that shows an embodiment of a light guiding element mounted near a scintillator in a digital radiographic detector according to the application. As illustrated in FIG. 3, a light guiding element 350 may also have two or more layers with different refractive indices in order to increase or maximize total internal reflection, reducing or minimizing optical loss and light leakage in the absence of scattering elements used to direct light out of the light guide. In one embodiment, the light guiding element 350 can include a top cladding layer 352 with refractive index n2, core layer 354 with refractive index n1, and bottom cladding layer 356 with refractive index n3. The optical index change in the light guiding element 350 may be abrupt, graded, linear and/or non-linear.

Figure 4:
FIG. 4 is a diagram that shows exemplary integrated beam detect including a light transfer unit embodiment positioned proximate a scintillator of radiographic imaging systems according to the application.

FIG. 4 is a diagram that shows an exemplary arrangement for a deposited scintillator. FIG. 4 shows exemplary integrated beam detect including a light transfer and photosensor unit embodiment positioned proximate a scintillator of radiographic imaging systems according to the application. A deposited scintillating layer 410, such as CsI, is typically deposited onto an imaging array 420, such as by vacuum evaporation. The imaging array 420 can be formed on a substrate 430. An encapsulation layer 412, such as Parylene$^R$, which can reduce or prevent moisture penetration is deposited to cover the vacuum deposited scintillating layer 410. A light guiding element 450 is placed in proximity to the encapsulation 412. Other scintillating layers 410, such as GOS, are comprised of particles of scintillator materials of 1 um-10 um in diameter, and can be blended with a binder material and coated onto the array, such as by knife-coating or slot-coating. An optional encapsulation layer 412 may be used to protect the GOS or coated scintillator. A light guiding element 450 is again is placed in proximity to the coated encapsulation 412. An output from the light guiding element 450 can be coupled to a photodetector 455.

The light guiding element 450 may be arranged proximate to the deposited scintillating layer and/or mixed particulate scintillating layer, for example, with optional encapsulation layer by one or more of an adhesive, by lamination using temperature and/or pressure, by an adhesive or by placing the light guiding element on the encapsulation with sufficient pressure to obtain uniform optical coupling.

Figure 5:
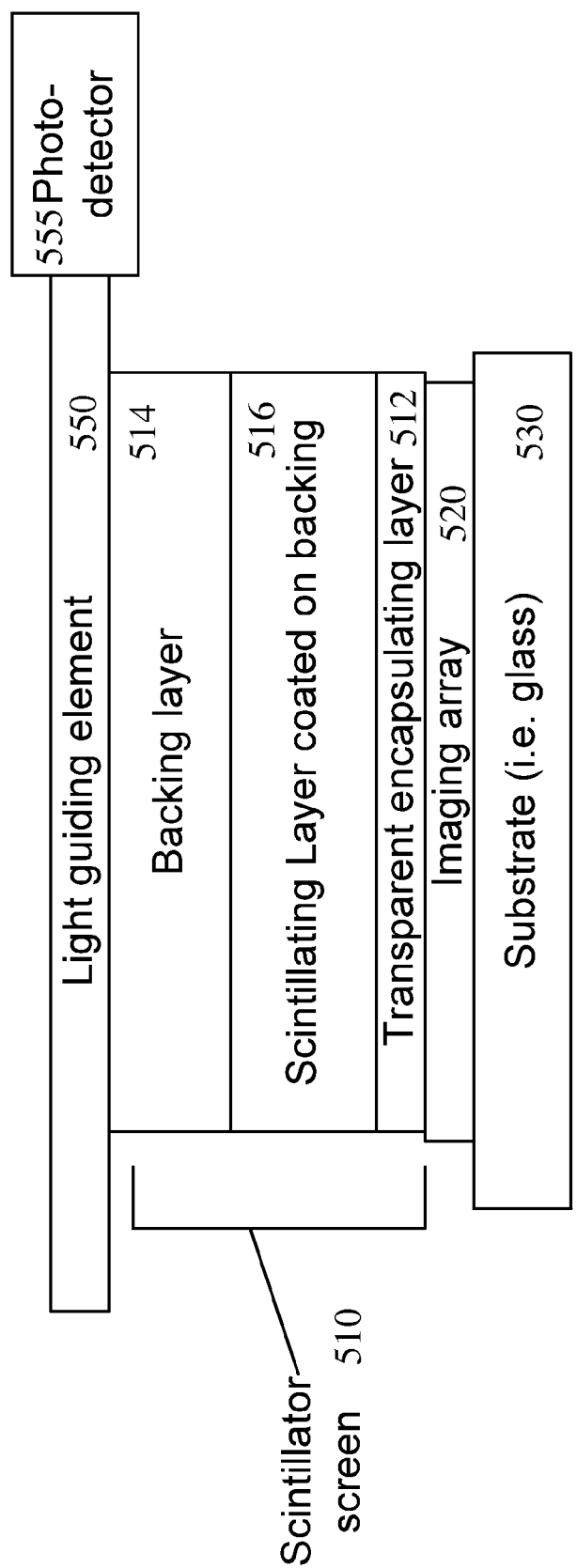
FIG. 5 is a diagram that shows exemplary integrated beam detect including a light transfer unit embodiment positioned proximate a scintillator of radiographic imaging systems according to the application.

FIG. 5 shows an exemplary arrangement for a scintillator screen attached to the imaging array. As shown in FIG. 5, an exemplary integrated beam detect including a light transfer and photosensor unit embodiment positioned proximate a scintillator of radiographic imaging systems according to the application. In this exemplary arrangement, a scintillator screen 510 can be formed of a particulate scintillator material, such as GOS coated with binder on a backing layer 514, such as polyester. The scintillator screen 510 may also include a transparent encapsulation layer 512 over the scintillating layer 516. Scintillator screens 510 may also be formed by vacuum deposition of a scintillator material, such as CsI, on a substrate 530, such as glass. The scintillating screen 510 may be placed proximate to an imaging array 520 by an adhesive (such as pressure sensitive adhesive) or by pressure contact. The imaging array 520 can be mounted on a substrate 530. A light guiding element 550 may be arranged proximate to the deposited scintillating layer with optional encapsulation layer, for example, by one or more of an adhesive, by lamination using temperature and/or pressure, by an adhesive or by placing the light guiding element on the encapsulation with sufficient pressure to obtain a selected or uniform optical coupling or the like. An output from the light guiding element 550 can be coupled to a photodetector 555.

Figure 6:
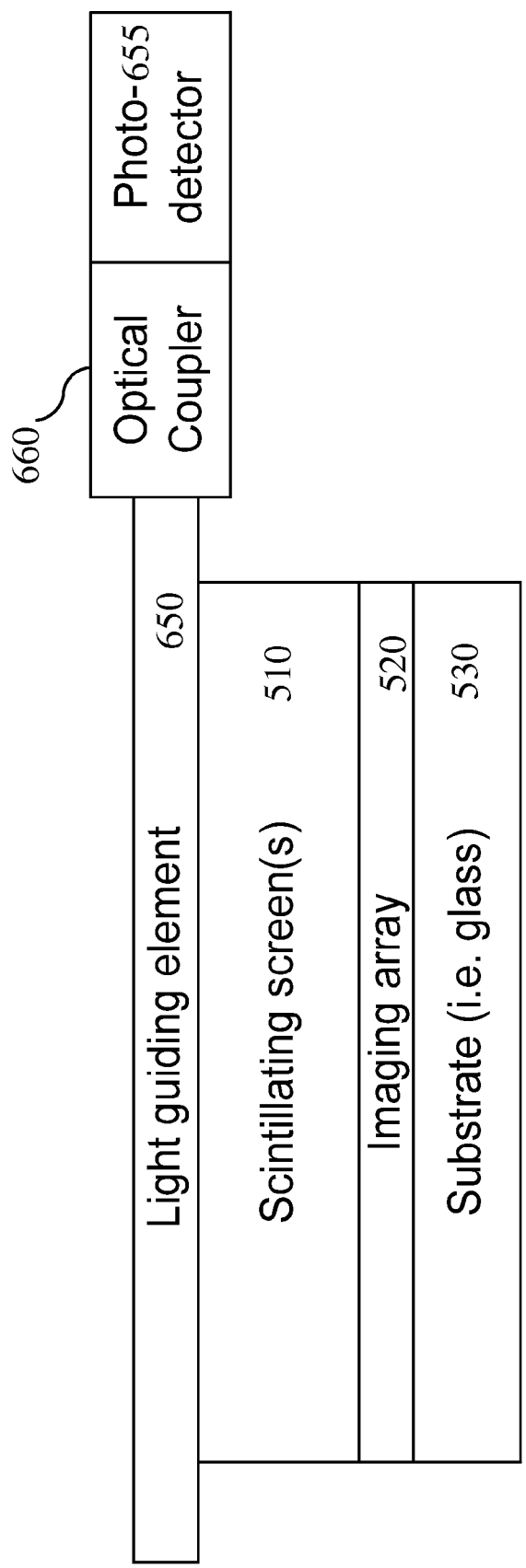
FIG. 6 is a diagram that shows an exemplary integrated beam detect including a light transfer and photosensor unit embodiment including an exemplary optical coupling element according to the application.

An optical coupling element can be inserted between a light guiding element and a photosensor. FIG. 6 shows exemplary integrated beam detect including a light transfer and photosensor unit embodiment including an exemplary optical coupling element. As shown in FIG. 6, an optical coupler 660 can be provided between a light guiding element 650 and photodetector 655. For certain exemplary embodiments, an optical coupling element such as the optical coupler 660 may comprise a lens, an optical fiber, one or more thin film optically coupling layers, one or more patterned reflectors, one or more patterned reflective layers patterned at sub-wavelength dimensions, one or more reflectors or the like.

Transmission between a scintillating screen and a light guiding element is a parameter to consider to control or optimize a radiographic imaging system such as a detector according to embodiments of the application. For example, a high optical coupling efficiency could allow a substantial portion of the light emitted from the scintillator screen to be lost to the light guiding element instead of the imaging array, which can reduce imaging array sensitivity to impinging X-rays. Alternatively, a low optical coupling efficiency between a scintillating screen and a light guiding element would not allow sufficient light to be transmitted into the light guiding element, which can result in failure of the photo-detector to detect the start-of-beam and/or the end-of-beam. Additionally, the photo-detector may receive insufficient light to estimate dose rate or total dose.

For certain exemplary embodiments, an optical coupling efficiency between a scintillating screen and a light guiding element, responsive to a location of the light guiding element, for example in the configuration of FIG. 5, may be controlled by a number of exemplary apparatus, conditions and/or methods described herein.

For certain exemplary embodiments, an index of refraction of a substrate of the scintillator support can be used to provide an optical coupling efficiency between a scintillating screen and a light guiding element. Thus, a proper choice of index of refraction of the support used in the scintillator screen and the index of refraction of the light guiding element can alter the optical coupling efficiency for a light guiding element. If the optical indexes of the scintillator screen and the light guide are the same, then the efficiency is 100%. Alternatively, as the optical index of the light guiding element decreases below that of an encapsulation layer, the optical coupling efficiency decreases. Thus, in one embodiment, the optical efficiency of light extraction can be controlled by choice of index of refraction of the scintillator substrate and light guide.

Figure 7:
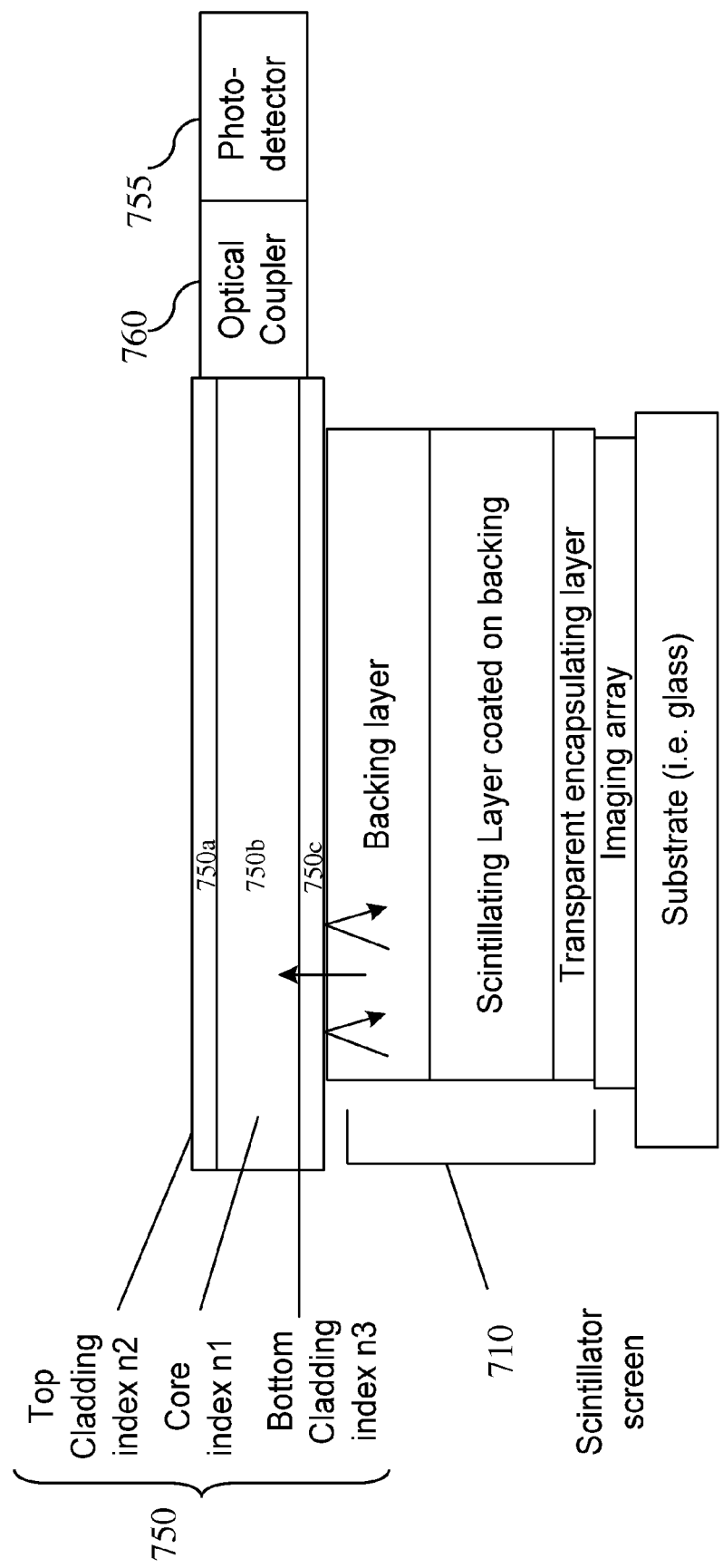
FIG. 7 is a diagram that shows an exemplary integrated beam detect including a light transfer and photosensor unit embodiment using index of refractions of a proximate scintillator support and a light guide, respectively, according to the application.

Cladding Layer with High Optical Index:

FIG. 7 is a diagram that shows an exemplary integrated beam detect including a light transfer and photosensor unit embodiment using index of refractions of a proximate scintillator support and a light guide, respectively, according to the application. As shown in FIG. 7, a light guide 750 can be formed of two or more layers 750a, 750b, 750c of optically transparent materials (e.g., core and cladding), where the optical index of the cladding layer 750c proximate the scintillator backing layer is higher than the optical index of the backing layer of the scintillator screen 710 and lower than the optical index of the core 750b. The transmission from the backing layer of the scintillator screen 710 to the light guide 750 can be tuned by appropriate choice of optical indices of the backing layer, the bottom cladding layer 750c and the core 750b. An output from the light guide 750 can be coupled to a photosensor 755 via an optical coupler 760.

A Patterned Reflection Layer

Figure 8:
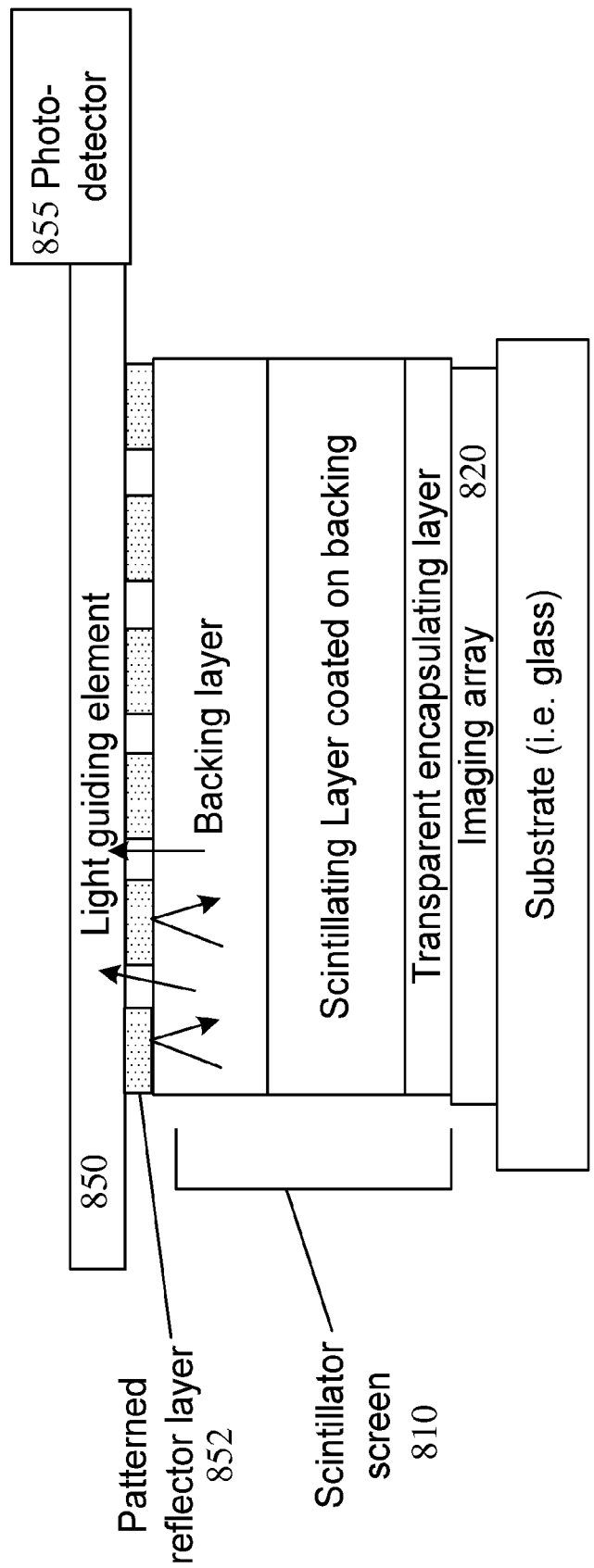
FIG. 8 is a diagram that shows an exemplary integrated beam detect including a light transfer and photosensor unit embodiment using patterned reflective layer according to the application.

FIG. 8 is a diagram that shows an exemplary integrated beam detect including a light transfer and photosensor unit embodiment using patterned reflective layer according to the application. As shown in FIG. 8, a patterned reflective layer 852 may be deposited or attached to the scintillating screen 810 in one embodiment. An example of a deposited reflection layer is shown in FIG. 8. The reflection layer 852 may include, for example, a metal such as aluminum. Holes patterned in the aluminum allow light to be transmitted from the substrate of the scintillator screen 810 into the light guiding element 850, where the optical coupling efficiency can depend on the size of the holes relative to the size of an imaging array 820. The reflective layer 852 can reflect light back into the scintillator screen 810 except where transparent regions (e.g., holes) are formed to allow the light rays to be transmitted there-through. In one embodiment, the patterned reflective layer 852 could also include a metallic grating with metal lines and spaces on a sub-wavelength pitch, and this patterned reflective layer would control transmission both by polarization selectivity and by optical coupling of the evanescent waves at the surface. An output from the light guide 850 can be coupled to a photosensor 855. In one embodiment, the reflective layer 852 can be part of the light guiding element 850.

Figure 9:
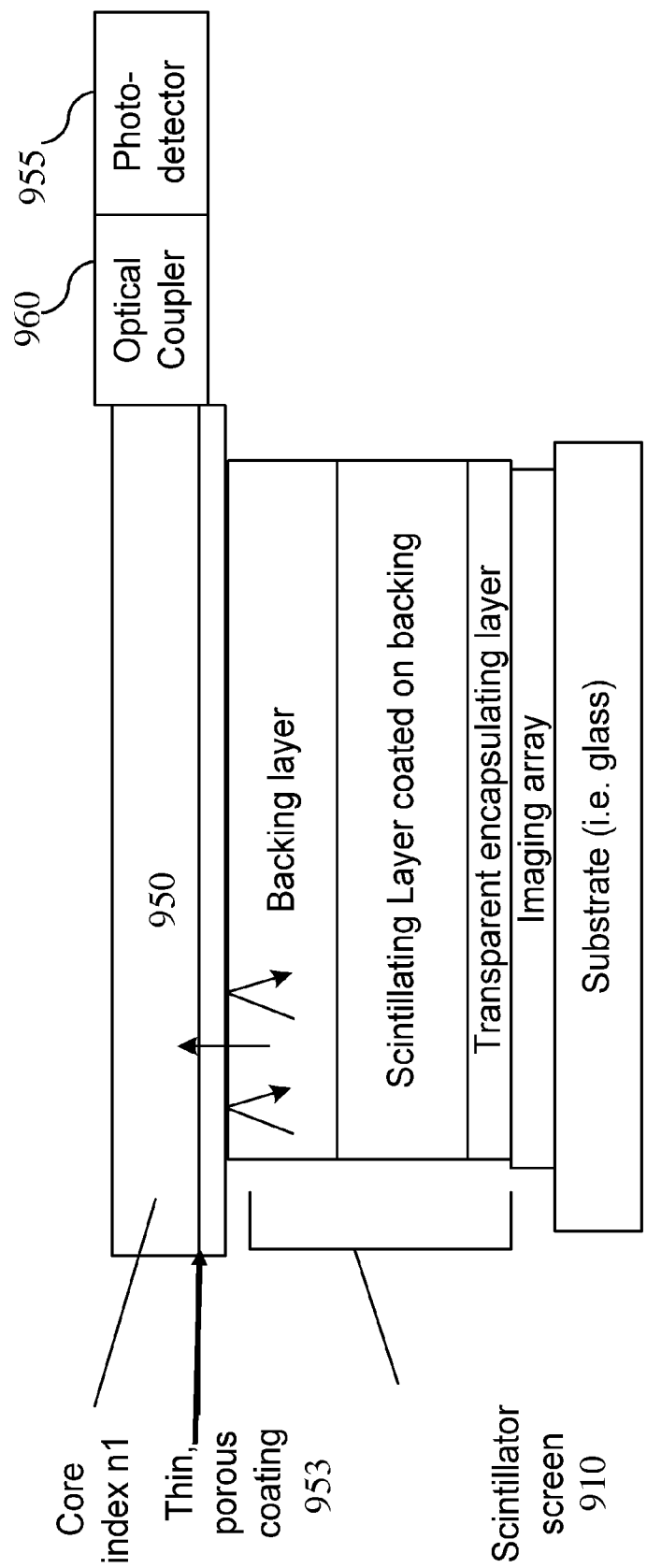
FIG. 9 is a diagram that shows an exemplary integrated beam detect including a light transfer and photosensor unit embodiment using a partially transmissive thin film according to the application.

Partially Transparent Thin Film:

FIG. 9 is a diagram that shows an exemplary integrated beam detect including a light transfer and photosensor unit embodiment using a partially transmissive thin film according to the application. As shown in FIG. 9, a partially transmissive thin film 953 may be positioned between a light guiding element 950 and a backing layer of a scintillator screen 910. In one embodiment a partially transmissive coating, such as a thin, porous film or the like can be used as the partially transmissive film 953. The partially transmissive film 953 may include, for example, of a very thin coating of particulate material, such as TiO2 or a very thin metal layer with incomplete coverage of the surface. An output from the light guide 950 can be coupled to a photosensor 955 via an optical coupler 960.

Embossed Surface on the Light Guide:

For certain exemplary embodiments, optical coupling can be modified by the presence of surface features in the light guide according to the application. For example, optical coupling with a scintillating screen and/or and imaging array can be modified by the presence of surface features in the light guiding element. In display backlight applications, surface topography can be used to scatter light out of the light guide into the LCD pixel. The density and/or size of the surface features can be used to adjust the extent of light extraction, and is usually patterned in a way to achieve uniform illumination over the display area for an edge-illuminated backlight. However, non-uniform illumination may be desirable for certain exemplary embodiments of light guiding elements described herein. Further, surface features on either surface of the light guide of a light guiding element embodiment can also be used to tune the optical transmission into the light guide.

Figure 10:
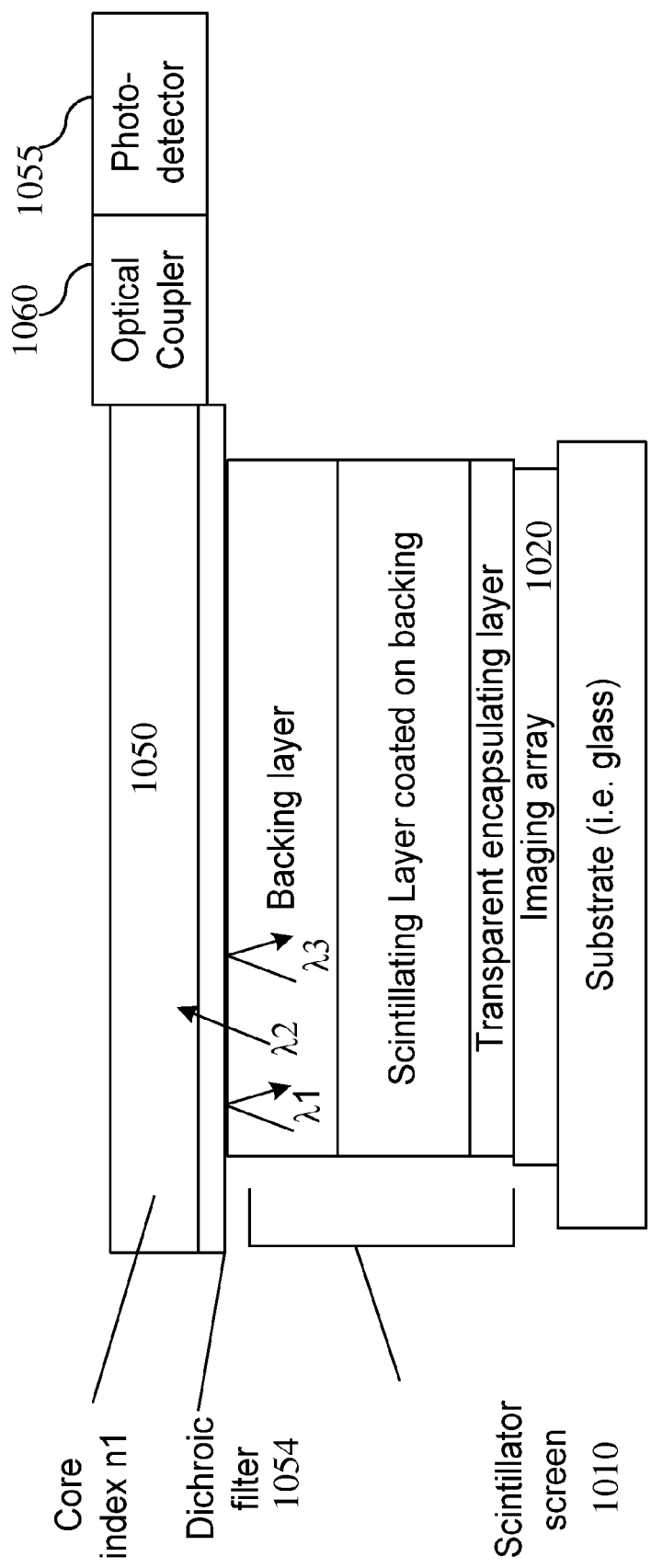
FIG. 10 is a diagram that shows an exemplary integrated beam detect including a light transfer and photosensor unit embodiment using a filter according to the application.

Wavelength Selectivity:

FIG. 10 is a diagram that shows an exemplary integrated beam detect including a light transfer and photosensor unit embodiment using a filter according to the application. Scintillator screens typically emit with spectra covering the visible and near UV wavelength range. The spectral distribution may be broad, as in the case of CsI scintillator screens, or have discrete emission lines, as in the case of GOS scintillator screens. A filter 1054 (e.g., dichroic filter or polarizing filter) positioned between a backing layer of the scintillator screen 1010 and the light guide 1050, as shown in FIG. 10, can allow transmission of some wavelengths of light and not others. By choosing the transmission curve of the filter 1054, the intensity of transmission from the scintillator screen 1010 to the light guide 1050 can be controlled.

Additionally, in one embodiment the transmission curve of the filter can be selected to maintain an imaging quality of an imaging array 1010. Imaging arrays have spectral response characteristics that can be higher at some wavelengths than at others. For example, amorphous silicon photodiodes used in flat panel imaging arrays typically have high quantum efficiency at wavelengths between 450 nm and 650 nm. The detector can have very low sensitivity to light emitted from scintillator screens outside of this 450-650 nm band. However, the photo-detectors 1055 attached to the light guide 1050 may be chosen to have high sensitivity to a much broader band of wavelengths. Single crystal silicon photodiodes, for example, have sensitivity out to 1,100 nm and also down to 300 nm. If a dichroic filter 1054 is tuned to selectively transmit light at wavelengths outside the high sensitivity band of the imaging array 1020 of the detector but still within the high sensitivity band of the photodiodes 1055 attached to the light guide 1050, the X-ray sensitivity of the imaging array 1020 is not reduced or significantly reduced by the presence of the light guide 1050. Control or optimization of the filter 1054 characteristics can be performed to achieve selected or maximum detection capability of the light guide 1050 and photo-detector 1055 via an optical coupler 1060 while reducing or minimizing sensitivity loss for X-ray imaging by the imaging array 1020.

Figure 11:
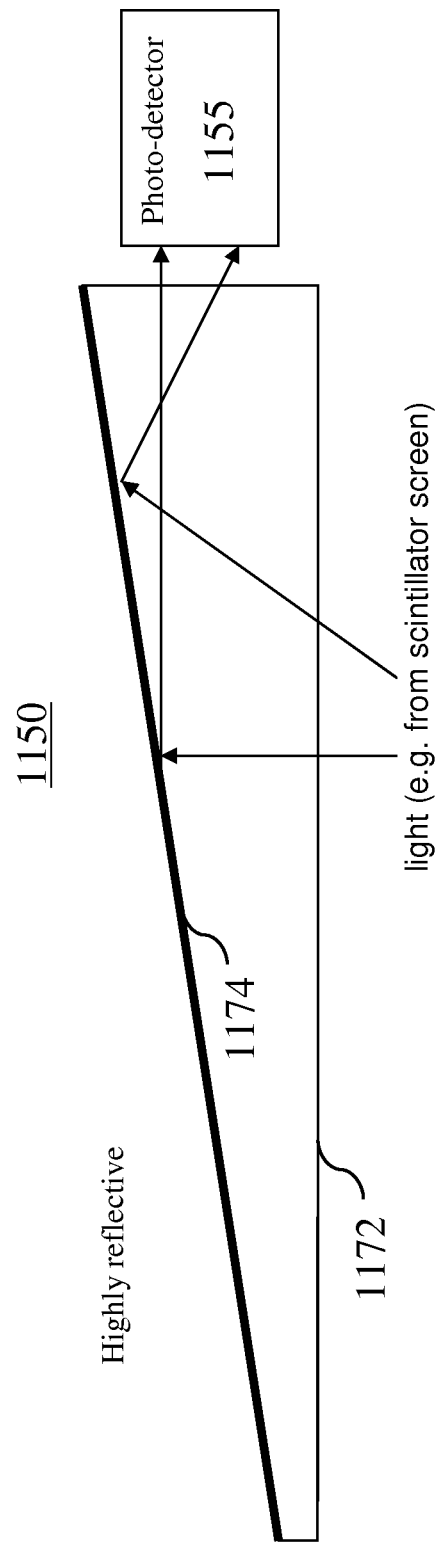
FIG. 11 is a diagram that shows an exemplary integrated beam detect including a light transfer and photosensor unit embodiment including a planar wedge reflective light guide according to the application.

Planar Wedge Reflective Light Guide:

FIG. 11 is a diagram that shows an exemplary integrated beam detect including a light transfer and photosensor unit embodiment including a planar wedge reflective light guide according to the application. As shown in FIG. 11, a light guiding element can be a planar wedge reflective light guide 1150 that can have a front planar surface 1172 (e.g., facing the scintillator screen) and a back angled surface 1174. The planar wedge reflective light guide 1150 can be made of optically clear materials such as acrylic resin, epoxies, glass, and the like. An inside or a first side of the back angled surface 1174 can be made reflective by a reflective coating, paint or the like. Light emitted by the scintillator screen (e.g., scintillator screen 1010) can enter the planar wedge reflective light guide 1150 through the front surface 1172 and can be reflected by the back angled surface 1174 to a photodetector 1155 positioned at the side of the planar wedge reflective light guide 1150. Because light emission from the scintillator is Lambertian, the size of the angle of the back angled surface 1174 is not critical; and a choice of angle is constrained more so by the available space. Further, a side of the planar wedge reflective light guide 1150 facing the photodetector 1155 may be treated with an anti-reflection coating to increase the light incident onto the photodetector 1155.

Figure 12:
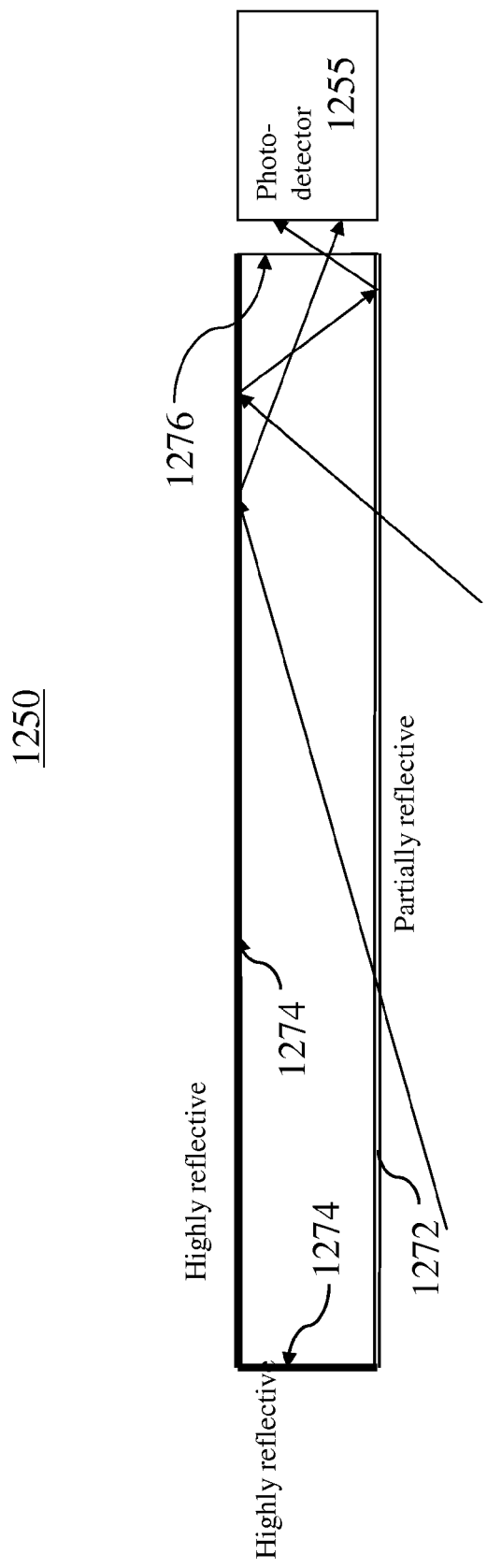
FIG. 12 is a diagram that shows an exemplary integrated beam detect including a light transfer and photosensor unit embodiment including a rectangular reflective light guide according to the application.

Rectangular Reflective Light Guide:

FIG. 12 is a diagram that shows an exemplary integrated beam detect including a light transfer and photosensor unit embodiment including a rectangular reflective light guide according to the application. As shown in FIG. 12, a light guiding element can be a rectangular reflective light guide 1250. The rectangular reflective light guide 1250 can be a planar light guide that can include a rectangular cross section and can be made of optically clear materials such as acrylic resin, epoxies, glass, and the like. In one embodiment, a side 1276 facing a photodetector 1255 can be left untreated or may be treated with an anti-reflection coating to increase or maximize light transmission. An input surface 1272, e.g., a surface facing the scintillator screen, can be made partially (e.g., 50%) reflective, such as by a dielectric coating. Preferably, all other surfaces 1274 of the rectangular reflective light guide 1250 are made highly reflective (e.g., by a reflective coating or paint). Some of the light emitted by the scintillator screen will enter the rectangular reflective light guide 1250, and by specular reflection, a portion of this light that entered the rectangular reflective light guide 1250 will exit the rectangular reflective light guide 1250 on the side into the photodetector 1255.

Figure 13:
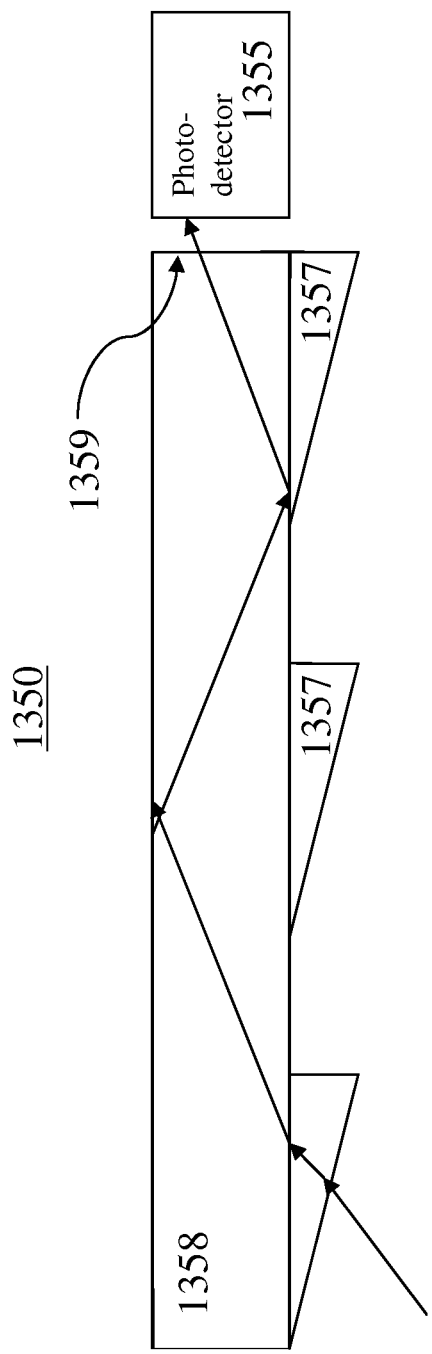
FIG. 13 is a diagram that shows an exemplary integrated beam detect including a light transfer and photosensor unit embodiment including microstructures according to the application.

Rectangular Light Guide with Micro-Prisms:

FIG. 13 is a diagram that shows an exemplary integrated beam detect including a light transfer and photosensor unit embodiment including microstructures according to the application. In one embodiment, a light guiding element 1350 can include a light guide with microstructures or light guide microstructures to control received light. In one embodiment, microstructures can include features such as micro-prisms. As shown in FIG. 13, a light guide 1350 with micro-prisms 1357 can include a planar slab 1358 having a rectangular cross section and an array of micro-prisms 1357 on one side (e.g., an input side), made of optically clear materials such as acrylic resin, epoxies, glass, and the like. A surface of the planar slab 1358 with the micro-prisms 1357 faces a scintillator screen. For illustration, only three micro-prisms 1357 are shown in FIG. 13. The micro-prisms 1357 can perform the function of coupling some of the light emitted from the scintillator screen into the planar slab 1358. The micro-prisms 1357 can be made of a material with a higher reflective index than that of the planar slab 1358. Not shown in FIG. 13 is a thin layer between the micro-prisms 1357 and the planar slab 1358 including air or another material with a smaller reflective index than that of the planar slab 1358. For certain exemplary embodiments, the planar slab 1358 can guide the coupled light to a photodetector 1355 (e.g., against one side 1359) through internal reflection (e.g., total internal reflection).

It can be seen by one skilled in the art that similar arrangements (e.g., for light guiding element embodiments shown in FIGS. 6-13) are possible for deposited scintillators with an encapsulation layer (e.g., illustrated in FIG. 4).

For certain exemplary embodiments, light guide element can be positioned in proximity to (e.g., below) a substrate of the radiographic imaging array. FIGS. 15A-15E are diagrams that show exemplary configurations for embodiments of light guide elements positioned near the substrate of the imaging array. Such embodiments can operate similarly to embodiments having light guiding elements positioned proximate to the scintillator screen described herein.

Figure 15A:
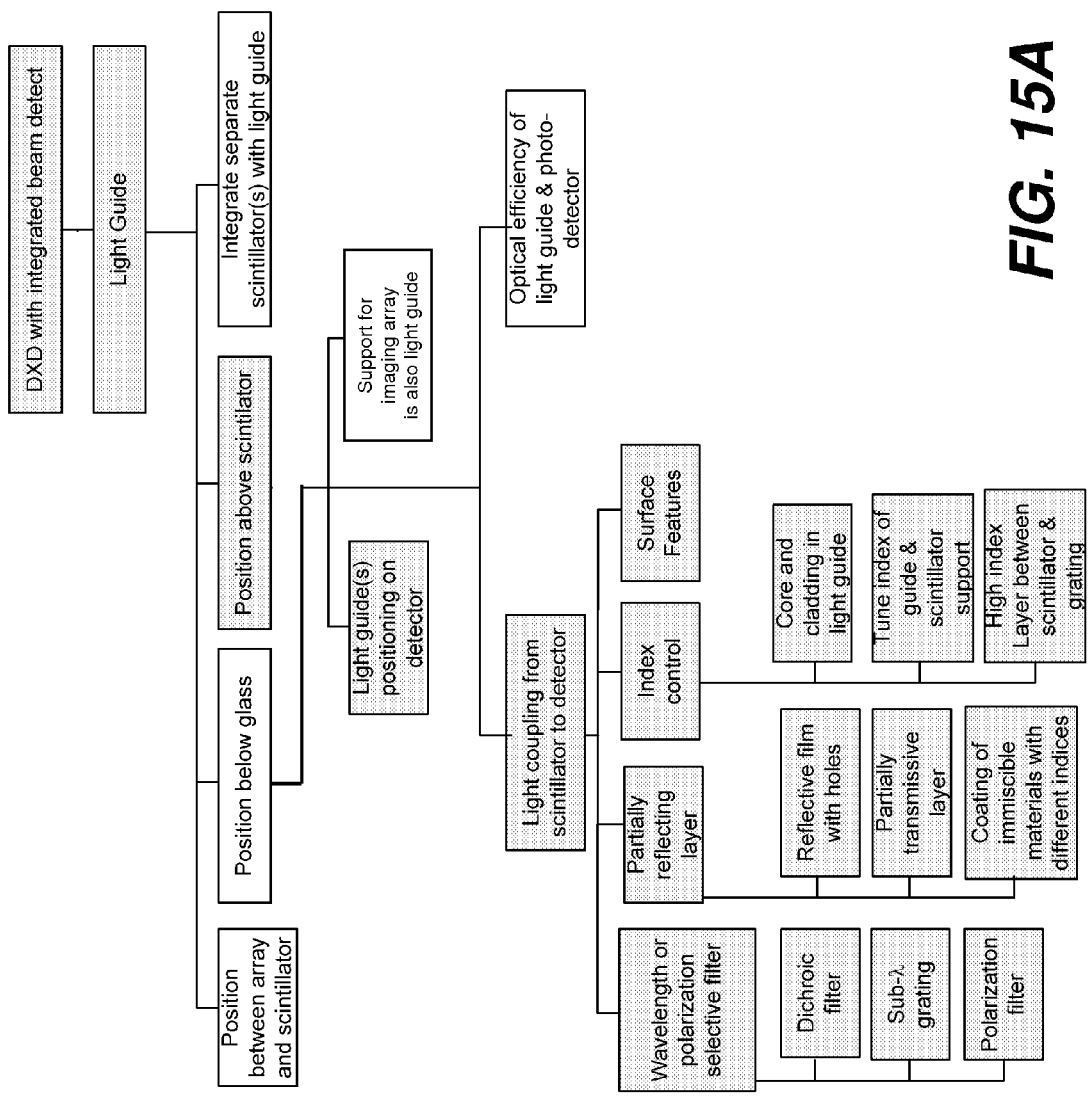
FIGS. 15A-15E are diagrams that show features of radiographic imaging systems including exemplary integrated beam detect including a light transfer unit positioned proximate imaging arrays according to the application.

FIG. 15A is a diagram that shows a chart of features of digital radiographic detectors including exemplary integrated beam detect including a light transfer unit proximate a substrate of an imaging array according to the application. As shown in FIG. 15A, light guiding element embodiments can be variously positioned below the glass of an imaging array or part of the support for the imaging array comprises part of light guiding element embodiments. Additional light guiding element embodiments can provide light coupling from the scintillator screen to light guiding element embodiments and from such light guiding element embodiments into a photosensor (e.g., photodetector). Further, as shown in FIG. 15A, light coupling from the scintillator screen though light guiding element embodiments to a photodetector can include wavelength or polarization selective filters, partially reflecting layers, index controls and/or surface features.

Figure 15B:
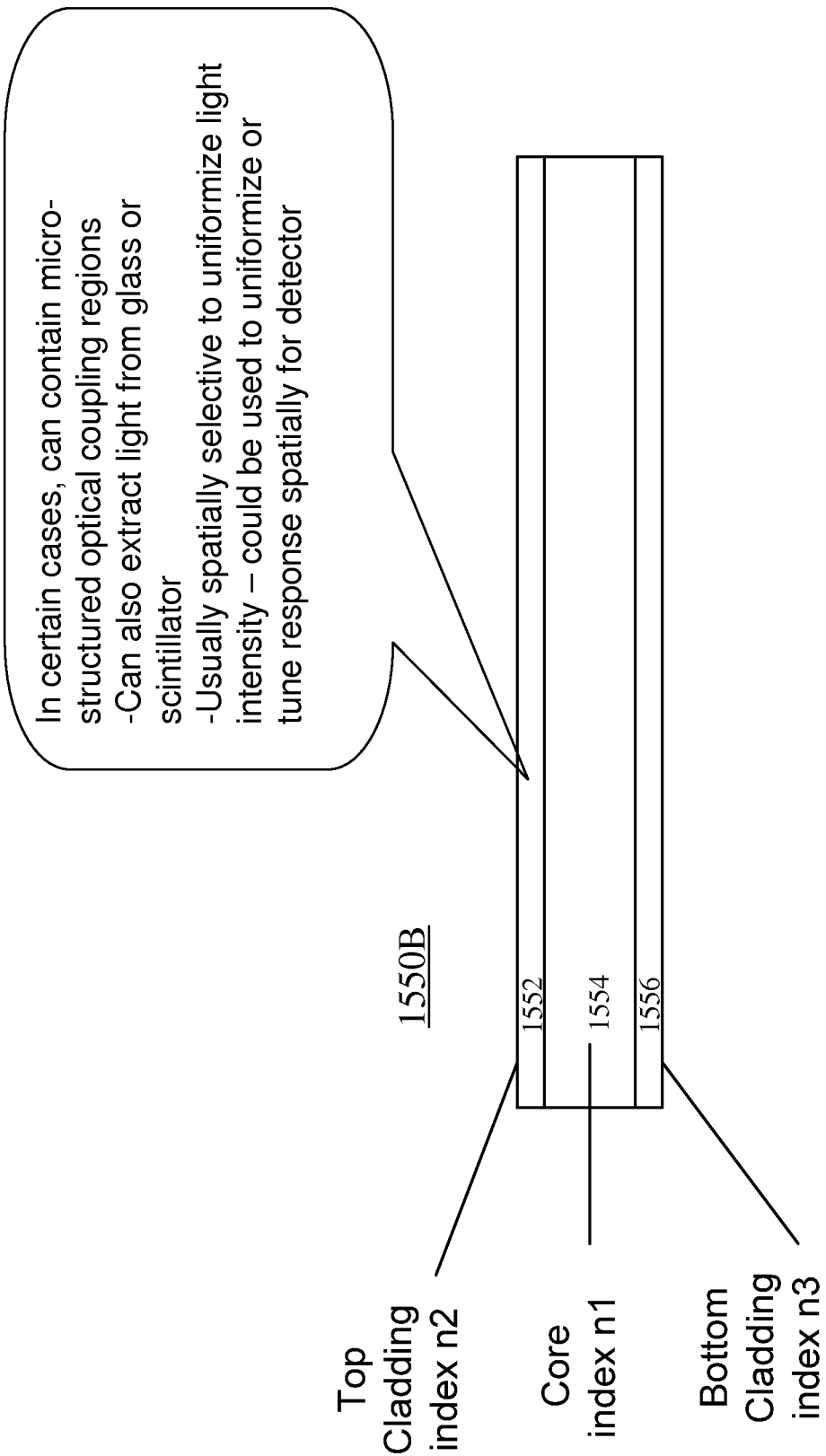
Figure 15C:
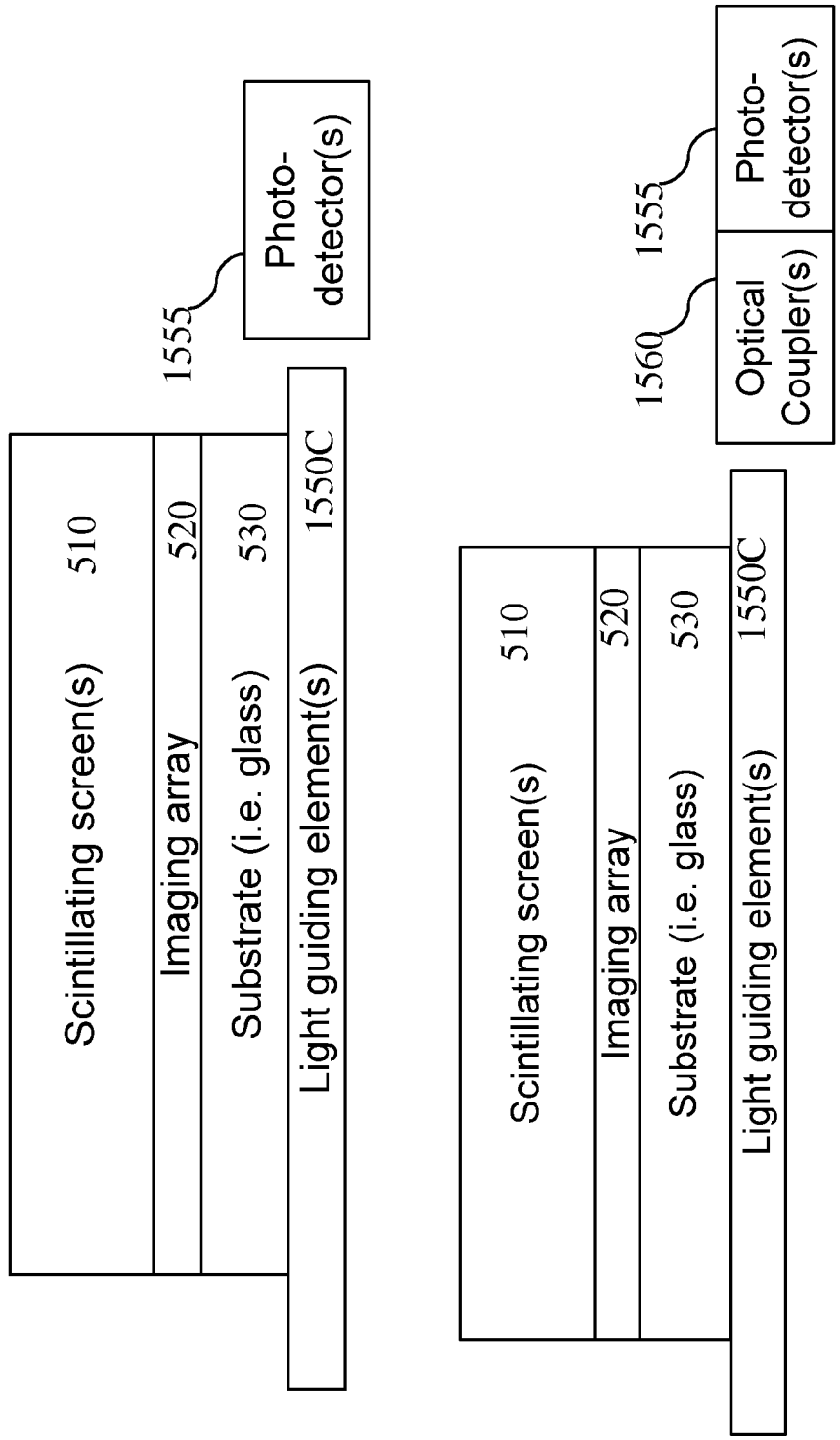

FIG. 15B is a diagram that shows an embodiment of a light guiding element to be mounted near a substrate (e.g., for an imaging array) in a digital radiographic detector according to the application. As illustrated in FIG. 15B, a light guiding element 1550B can include a top cladding layer 1552 with refractive index n2, core layer 1554 with refractive index n1, and bottom cladding layer 1556 with refractive index n3. In certain exemplary embodiments, the light guiding element 1550B, can contain micro-structured optical coupling regions, can be configured to extract light from transparent support (e.g., imaging array or scintillator), or can be spatially selective to light intensity (e.g., to increase or make uniform, or tune response spatially) for detector. FIG. 15C shows exemplary integrated beam detect including a light transfer and photosensor unit embodiment positioned proximate a support of an imaging array of radiographic imaging systems according to the application. As shown in FIG. 15C, an output from a light guiding element 1550C can be coupled to a photosensor such as a photodetector 1555. Alternatively, an optical coupler 1560 can be provided between a light guiding element 1550C and photodetector 1555. For certain exemplary embodiments, an optical coupling element such as the optical coupler 1560 may comprise a lens, an optical fiber, one or more reflectors or the like.

Figure 15D:
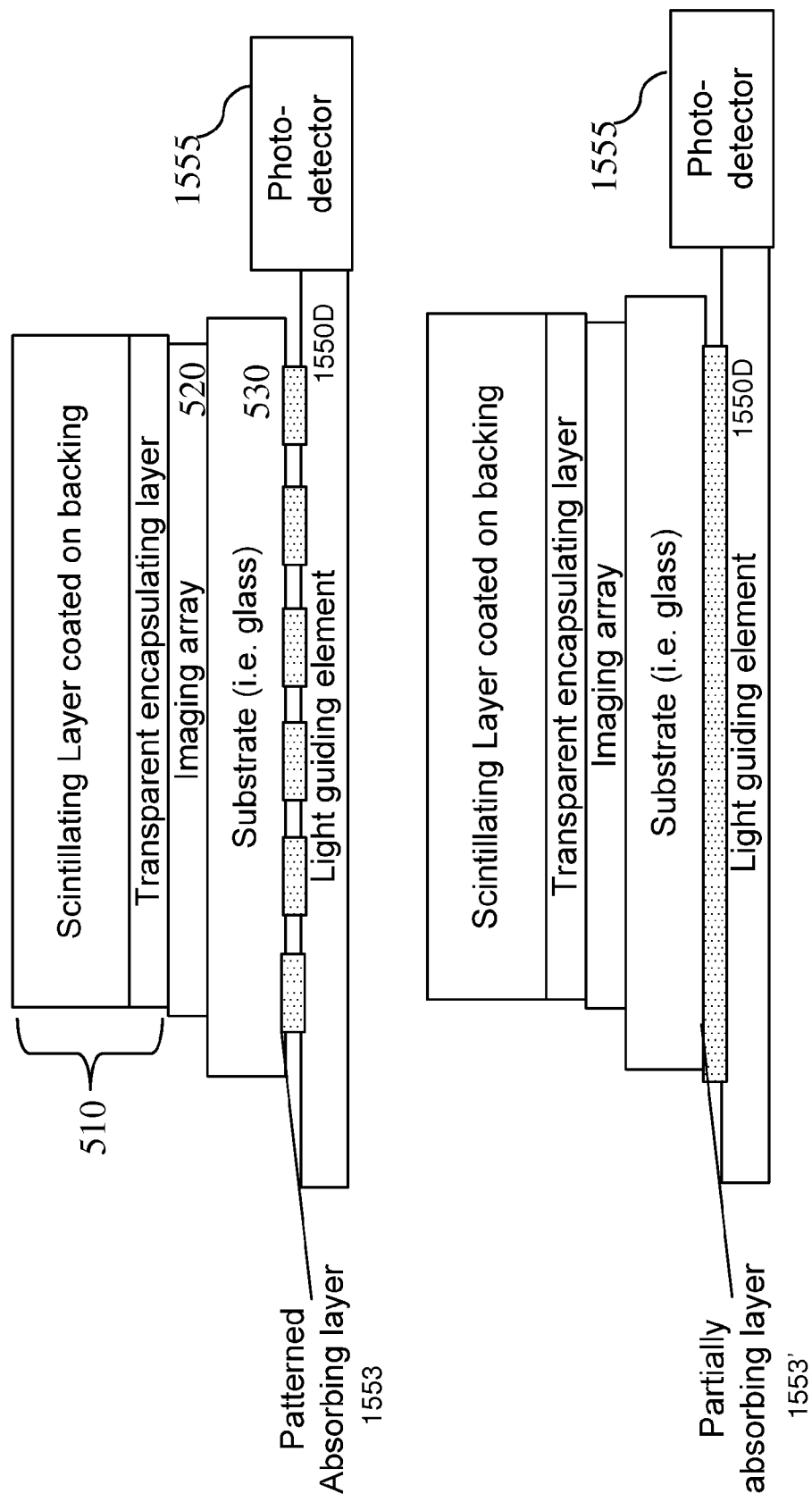

FIG. 15D is a diagram that shows an exemplary integrated beam detect including a light transfer and photosensor unit embodiment using an absorbing material according to the application. As shown in FIG. 15D, a patterned absorbing layer 1553 or partially absorbing layer 1553' can transfer light passing through the imaging array to a light guiding element 1550D coupled to a photodetector 1555.

Figure 15E:
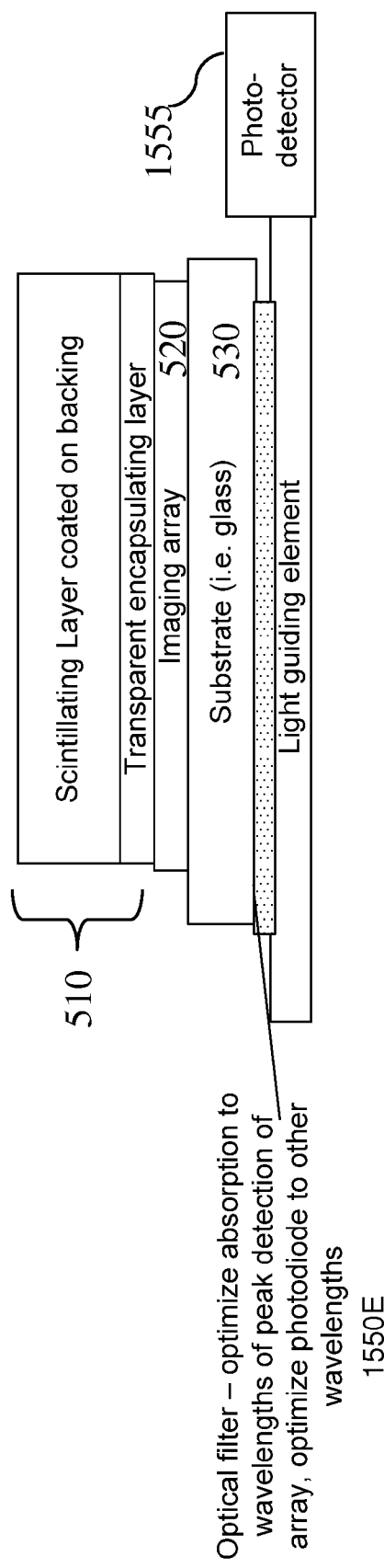

FIG. 15E is a diagram that shows an exemplary integrated beam detect including a light transfer and photosensor unit embodiment using an optical filter according to the application. A light guiding element including an optical filter 1550E can be positioned below the substrate to transfer light (e.g., control reflection and transmission) from the scintillator screen 510 to the photodetector 1555. In one embodiment, the imaging array 520 can be optimized for a wavelength or wavelength range and the photodetector 1555 can be optimized to a different wavelength or wavelength range emitted by the scintillator screen 510.

Figure 16:
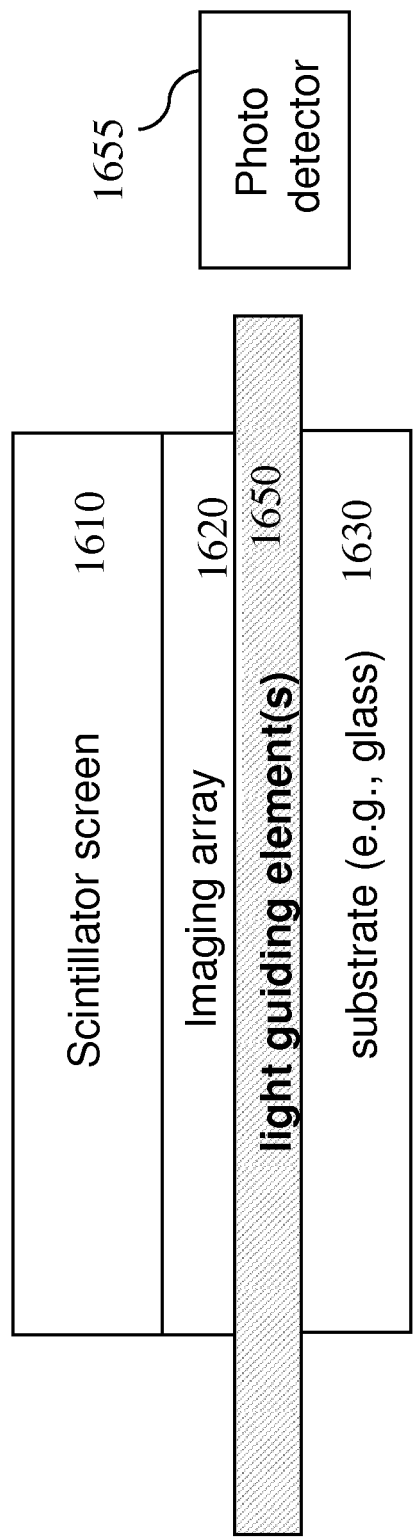
FIG. 16 is a diagram that shows features of radiographic imaging systems including exemplary integrated beam detect including a light transfer unit positioned between an imaging array and a substrate of the imaging array according to the application.

For certain exemplary embodiments, light guide element can be positioned in proximity to the radiographic imaging array. FIG. 16 is a diagram that shows exemplary configurations for embodiments of light guide elements positioned between the imaging array and a substrate of the imaging array. As shown in FIG. 16, light guiding element 1650 is between a substrate 1630 of an imaging array 1620 for coupling light from a scintillator screen 1610 to a photodetector 1655. Such embodiments can operate similarly to embodiments having light guiding elements positioned proximate to the scintillator screen described herein.

Figure 17A:
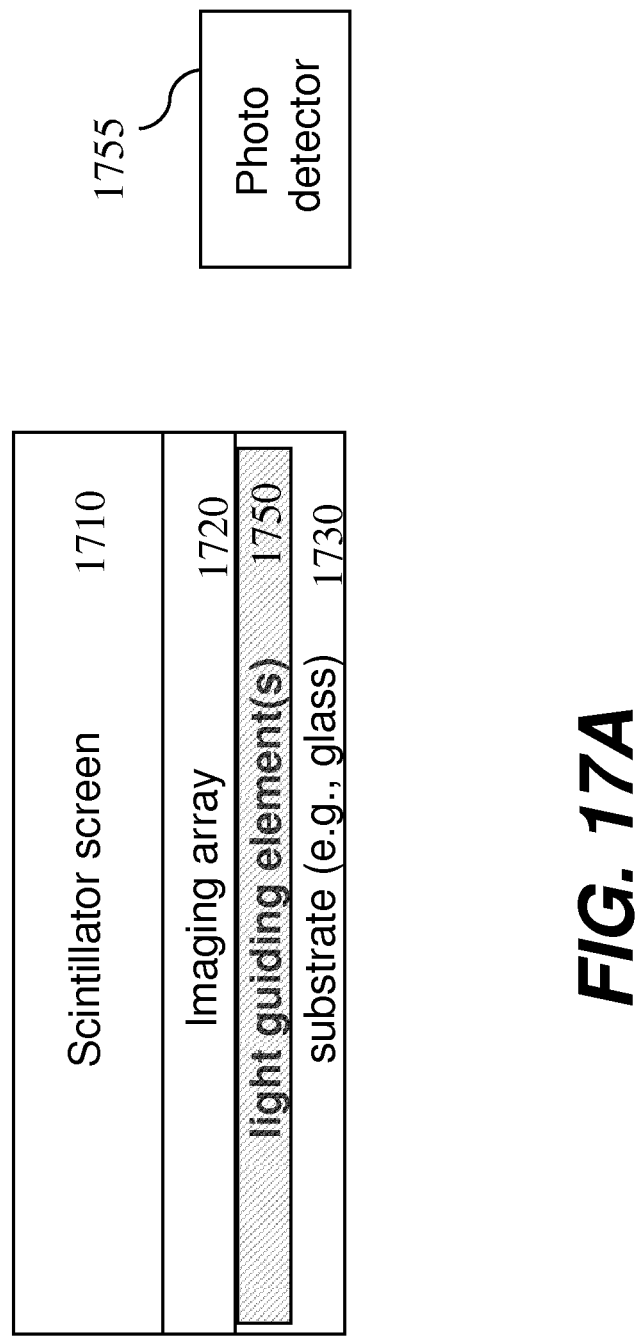
FIGS. 17A-17B are diagrams that show features of radiographic imaging systems including exemplary integrated beam detect including a light transfer unit positioned in imaging array substrates according to the application.
Figure 17B:
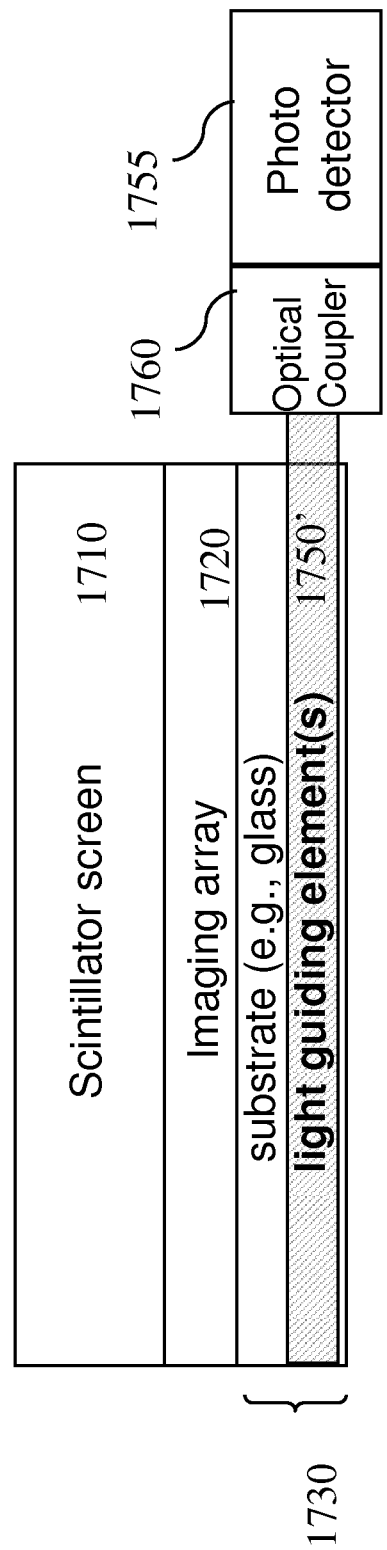

Certain exemplary embodiments can implement a light guiding element as a portion of a support for a scintillator screen and/or a portion of a substrate for the radiographic imaging array. Embodiments of a light guiding element can be contained within the support or substrate, extend throughout the support or substrate or extend beyond the support or substrate and be operationally coupled to a photosensor or photodetector. FIGS. 17A-17B are diagrams that show exemplary integrated beam detect including a light transfer and photosensor unit embodiments implemented at a substrate for the radiographic imaging array according to the application. As shown in FIG. 17A, light guiding element 1750 is contained within a substrate 1730 of an imaging array 1720 for coupling light from a scintillator screen 1710 to a photodetector 1755. As shown in FIG. 17B, light guiding element 1750' embedded in substrate 1730 extends beyond to be connected to photodetector 1755 through an optical coupler 1760 for coupling light from a scintillator screen 1710 to a photodetector 1755. In one embodiment micro-structures can be implemented in the support for a scintillator screen or the substrate for the radiographic imaging array. For such embodiments, exemplary microstructures can perform the function of coupling some of the light emitted from the scintillator screen into the light guiding element for detection by the spaced apart photo-detector. For example, such microstructures can include but are not limited to micro-prisms, wedges, stacked prescribed refractive layers or the like.

Figure 18:
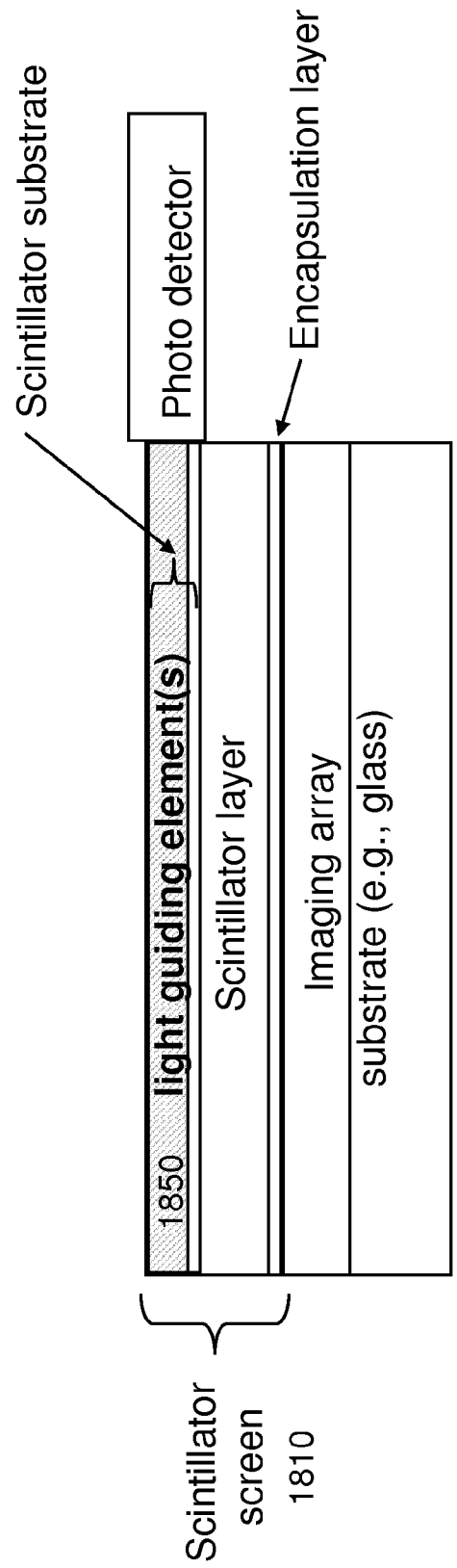
FIG. 18 is a diagram that shows features of radiographic imaging systems including exemplary integrated beam detect including a light transfer unit positioned in a scintillator substrate according to the application.

FIG. 18 is a diagram that shows features of radiographic imaging systems including exemplary integrated beam detect including a light transfer unit positioned in a scintillator substrate according to the application. As shown in FIG. 18, a scintillator screen 1810 comprises an embodiment of a light guiding element 1850.

In some cases, low-resolution spatial information about the total dose and/or dose rate may be of interest. In such cases separate light guides may be provided for different spatial locations on the detector. For example, the corner or edge regions are frequently subject to the unattenuated X-ray beam, such as outside the body wall in a chest X-ray. These regions would give high signal-to-noise for the photo-detector. Other regions, such as in the center of the detector, are subject to attenuation from the person or object being imaged. Measuring dose rate and integrated dose can be useful to determining if sufficient exposure has been used to provide good signal-to-noise ratio in the detector. The low-resolution spatial monitoring of X-ray exposure can be achieved by placing separate light guides over selected areas of the scintillator, each with individual photo-detectors, as illustrated in FIG. 14.

Thus, certain exemplary embodiments can include a plurality of prescribed light guides, each of which can have a preset shape (e.g., the same or different) and be coupled to a different photo-detector to monitor dose rate or integrated dose. In one embodiment, the preset shape can mimic a known AEC configuration. In one embodiment, the light guiding element can include a plurality of independent non-overlapping light guides (e.g., see FIG. 14). Thus, separate light guide embodiments can be positioned over various portions of the detector array to provide individual monitoring of X-ray exposure in various regions of the detector.

Exemplary embodiments can include combinations of features described herein.

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

Methods/apparatus embodiments of a digital radiographic (DR) detector can be configured to use a light guiding element to redirect light for detection of one or more of (a) the start of exposure, (b) the intensity of exposure (c) the end of exposure and (d) the total dose, and/or (e) dose and/or dose rate vs. x-y position on the detector. In certain exemplary embodiments, the use of such information generated by the light guiding element embodiments can be to change operating modes or operating conditions at the DR detector. In some exemplary embodiments, such changed operating modes or operating conditions at the DR detector responsive to information generated by the light guiding element embodiments can include but are not limited to operating states (e.g., examination based imaging, high speed imaging, low power imaging, radiographic imaging), power states (e.g., full power, standby power, low power, automatic x-ray exposure state), timing modes (e.g., standard refresh, high rate timing, reduced rate timing, low power timing, adjusted clock speed modes), readout modes, power modes (e.g., digital logic circuits powered off, battery power schemes), power refresh. In certain exemplary embodiments, the light guiding element is independent of the imaging array (e.g., not part of a pixel, a semiconductor layer, a semiconductor layer of the pixel or a semiconductor layer of the radiographic imaging array, etc.) to which a scintillating screen is attached. In one embodiment, the light guiding element is proximate the scintillator screen or positioned on a second side of the scintillating screen opposite a first side of the scintillator screen proximate the imaging array. In one embodiment, the light guiding element is proximate the imaging array or positioned on a second side of the imaging array opposite a first side of the imaging array proximate the scintillator screen. In one embodiment, the imaging array comprises a substrate to support the imaging array, where the light guiding element is proximate the substrate or positioned on a second side of the substrate opposite a first side of the substrate proximate the imaging array. In one embodiment, the imaging array comprises a substrate to support the imaging array, where the light guiding element is between the substrate and the imaging array. In one embodiment, the detector comprises a substrate to support the imaging array or the scintillator screen comprises a backing layer, where the substrate or the backing layer comprises the light guiding element.

In one embodiment, the light guiding element is a light collection film, an optical film, an optical plate, a single sheet, a plate of optically transparent material, comprises a micro-structured light control element, a micro-structured prism, or a wedge shaped optical transmission element. In one embodiment, the light guiding element uses internal reflection to propagate a portion of received light to a selected detection point or exit of the light guiding element. In one embodiment, light guiding element comprises two or more layers each including different refractive indices to control internal reflection, reduce optical loss and/or reduce light leakage in the absence of scattering elements used to direct light out of the light guide, where an optical index change between layers or along a direction in one layer is abrupt, gradual, linear, nonlinear or tiered. In one embodiment, the light guiding element is configured to guide received light to at least one light detection element. In one embodiment, the light guiding element is configured to extract a portion of the light from the scintillator screen and guide the extracted light to at least one light detection element. In one embodiment, the at least one light detection element is on a periphery of the scintillator screen or a perimeter of the imaging array. In one embodiment, an optical coupling element can be between the light guiding element and the light detection element, where the optical coupling element comprises a lens, an optical fiber, or one or more reflectors.

In one embodiment, the scintillator screen is deposited directly onto the imaging array, the scintillator screen is laminated to the imaging array, the scintillator screen attached to the imaging array, the scintillator screen adhesively coupled to the imaging array, or the scintillator screen is held in contact with the imaging array. In one embodiment, the scintillator screen comprises CsI or GOS. In one embodiment, the detector comprises an encapsulation layer for the scintillator screen, where the light guiding element is proximate the encapsulation layer. In one embodiment, the scintillator screen comprises a substrate and scintillating material attached to the substrate, where the light guiding element is proximate the scintillator screen substrate.

In one embodiment, the detector comprises an optical transmission control element adjacent to the light guiding element, where the optical transmission control element passes sufficient light to detect the start-of-beam, to detect the end-of-beam, to estimate dose rate and/or estimate total dose. In one embodiment, the optical transmission control element passes less than 10% of light, less than 30% of light or less than 50% of light generated by the scintillator screen. In one embodiment, the optical transmission control element passes a portion of light generated by the scintillator screen. In one embodiment, the optical transmission control element passes a wavelength of light not detected or not substantially detected by the detector imaging array. In certain exemplary embodiments, not detected is intended to mean not intentionally detected or not substantially detected. In one embodiment, the optical transmission control element comprises index of refraction of the substrate and light guide. In one embodiment, the optical transmission control element comprises first index of refraction of the scintillator screen or a substrate of the scintillator screen and a second index of refraction of the light guide. In one embodiment, the optical transmission control element comprises a backing layer of the scintillator screen, a bottom cladding layer of the light guiding element, at least one core layer of the light guiding element or a top cladding layer of the light guiding element, where respective indices of refraction of the backing layer, the bottom cladding layer, the at least one core layer or the top cladding layer are used to control transmission from the scintillator screen to the light detection element through the light guiding element. In one embodiment, the optical transmission control element comprises a patterned reflecting layer or a partially transmissive thin film between a backing layer of the scintillator screen and the light guiding element. In one embodiment, the optical transmission control element comprises surface features on at least one surface of the light guiding element to tune optical transmission into the light guiding element. In one embodiment, the optical transmission control element comprises a filter positioned between the scintillator screen and the light guiding element, where a transmission curve of the filter is configured to control the intensity of transmission from the scintillator screen to the light guiding element. In one embodiment, the optical transmission control element comprises a dichroic filter positioned between the scintillator screen and the light guiding element to pass a first bandwidth of light not detectable by the imaging array, where the first bandwidth of light is detectable by the light detection element.

In one embodiment, the detector can include a light guiding element that comprises a plurality of light guides each corresponding to different spatial locations of the imaging array or DR detector, and where the light detection element comprises a plurality of light detectors each corresponding to one of the plurality of light guides. In one embodiment, the detector can include separate light guides over selected areas of the scintillator screen; and individual photo-detectors coupled to each of the separate light guides. In one embodiment, the light detection element comprises photodetectors, photodiodes or the like.

In one embodiment, the imaging array comprises a substrate to support the imaging array, where the substrate is transparent, or where the substrate comprises glass or plastic. In one embodiment, the scintillator screen comprises a substrate, where the substrate is transparent, or where the substrate comprises glass or plastic.

In one embodiment, an automatic exposure control (AEC) capability of the DR detector is configured to use the dose of the exposure dose or the rate of dose.

In one embodiment, a radiation image capturing device can include an image capturing unit to capture a radiation image using irradiated radiation; a radiation detection unit that detects the radiation; a determination unit to determine whether image capturing preparation is completed; and a control unit to start detection of the radiation by the radiation detection unit, in a case in which the determination unit determines that the image capturing preparation is completed, and controls the image capturing unit to capture a radiation image, in a case in which the radiation detection unit detects the radiation, where the radiation detection unit comprises a layer of light guiding material within the image capturing unit configured to transfer light generated by a scintillator of the image capturing unit outside an exposure area of the radiation image for the detection of the radiation. In one embodiment, the light guiding material is a layer proximate to one of the scintillator, a radiographic imaging array or a substrate of the imaging array. In one embodiment, the image capturing unit comprises a radiographic imaging array including a substrate to support the radiographic imaging array and a scintillator screen including a backing layer, where the substrate or the backing layer comprises a light guiding material. In one embodiment, the material is a light guiding element comprising an optical film, an optical layer, an optical plate, a microstructured light control element, a micro-structured prism, or a wedge shaped optical transmission element.

Priority is claimed from commonly assigned, copending U.S. provisional patent application Ser. No. 61/698,573, filed Sep. 8, 2012, entitled "RADIOGRAPHIC IMAGING SYSTEMS INCLUDING SCINTILLATOR SCREEN WITH INTEGRATED BEAM DETECT", in the name of Timothy J. Tredwell et al., the disclosure of which is incorporated by reference.

In addition, while a feature(s) of the invention can have been disclosed with respect to at least one of several implementations/embodiments, such feature can be combined with one or more other features of other implementations/embodiments as can be desired and/or advantageous for any given or identifiable function. To the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items can be selected. Further, in the discussion and claims herein, the term "exemplary" indicates the description is used as an example, rather than implying that it is an ideal.

The invention has been described in detail with particular reference to exemplary embodiments, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A digital radiography detector comprising:
a housing having first and second spaced planar members and side walls defining a cavity;

a radiographic image detector assembly mounted within the cavity for converting a radiographic image to an electronic radiographic image, wherein the detector assembly includes a scintillator screen and a detector imaging array; and a light guiding element positioned proximate the radiographic image detector assembly to redirect light for detection of any one or more of a start of an exposure, a termination of the exposure, a dose for the exposure, or a rate of dose for the exposure, using light generated by the scintillator screen, wherein the light guiding element is not included in the detector imaging array or included in a semiconductor layer of the detector imaging array.

2. The digital radiography detector of claim 1, where the light guiding element is proximate the scintillator screen or positioned on a second side of the scintillating screen opposite a first side of the scintillator screen proximate the imaging array.

3. The digital radiography detector of claim 1, where the imaging array comprises a substrate to support the imaging array or the scintillator screen comprises a backing layer, where the substrate or the backing layer comprises the light guiding element.

4. The digital radiography detector of claim 1, where the light guiding element is a light collection film, an optical film, an optical plate, a single sheet, a plate of optically transparent material, comprises a microstructured light control element, a micro-structured prism, or a wedge shaped optical transmission element.

5. The digital radiography detector of claim 1, where the light guiding element uses internal reflection to propagate a portion of received light to a selected detection point or exit of the light guiding element.

6. The digital radiography detector of claim 1, where the light guiding element is configured to extract a portion of the light from the scintillator screen and guide the extracted light to at least one light detection element, where the at least one light detection element is on a periphery of the scintillator screen or a perimeter of the imaging array.

7. The digital radiography detector of claim 1, comprising an optical coupling element between the light guiding element and the light detection element, where the optical coupling element comprises a lens, an optical fiber, one or more reflectors.

8. The digital radiography detector of claim 1, where the light guiding element comprises a plurality of light guides each corresponding to different spatial locations of the imaging array or DR detector, and where the light detection element comprises a plurality of light detectors each corresponding to one of the plurality of light guides.

9. The digital radiography detector of claim 8, comprising:
separate light guides over selected areas of the scintillator screen; and
individual photo-detectors coupled to each of the separate light guides.

10. The digital radiography detector of claim 8, comprising:
separate light guides coupled at substrates of the imaging array; and
individual photo-detectors coupled to each of the separate light guides.

11. A digital radiography detector comprising:
a housing having first and second spaced planar members and side walls defining a cavity;
a radiographic image detector assembly mounted within the cavity for converting a radiographic image to an electronic radiographic image, wherein the detector assembly includes a scintillator screen and a detector imaging array; and
a light guiding element positioned proximate the radiographic image detector assembly to redirect light for detection of any one or more of a start of an exposure, a termination of the exposure, a dose for the exposure, or a rate of dose for the exposure, using light generated by the scintillator screen, wherein the light guiding element comprises two or more layers each including different refractive indices to control internal reflection, reduce optical loss and/or reduce light leakage in the absence of scattering elements used to direct light out of the light guide, where an optical index change between layers or along a direction in one layer is abrupt, gradual, linear, nonlinear or tiered.

12. A digital radiography detector comprising:
a housing having first and second spaced planar members and side walls defining a cavity;
a radiographic image detector assembly mounted within the cavity for converting a radiographic image to an electronic radiographic image, wherein the detector assembly includes a scintillator screen and a detector imaging array;
a light guiding element positioned proximate the radiographic image detector assembly to redirect light for detection of any one or more of a start of an exposure, a termination of the exposure, a dose for the exposure, or a rate of dose for the exposure, using light generated by the scintillator screen; and
an optical transmission control element adjacent to the light guiding element, where the optical transmission control element passes sufficient light to detect the start-of-beam, to detect the end-of-beam, to estimate dose rate and/or estimate total dose.

13. The digital radiography detector of claim 12, where the optical transmission control element passes a wavelength of light not substantially detected by the detector imaging array.

14. The digital radiography detector of claim 12, where the optical transmission control element comprises surface features on at least one surface of the light guiding element to tune optical transmission into the light guiding element.

15. The digital radiography detector of claim 12, where the optical transmission control element comprises a filter positioned between the scintillator screen and the light guiding element, where a transmission curve of the filter is configured to control one of wavelength or the intensity of transmission from the scintillator screen to the light guiding element.

16. A radiation image capturing device comprising:
an image capturing unit comprising an imaging array and a scintillator, the image capturing unit to capture a radiation image using irradiated radiation;
a radiation detection unit that detects the radiation;
a determination unit to determine whether image capturing preparation is completed; and
a control unit to start detection of the radiation by the radiation detection unit, in a case in which the determination unit determines that the image capturing preparation is completed, and controls the image capturing unit to capture the radiation image, in a case in which the radiation detection unit detects the radiation,
where the radiation detection unit comprises a layer of light guiding material within the image capturing unit but not included in the imaging array, the radiation detection unit configured to transfer light generated by the scintillator of the image capturing unit for the detection of the radiation.

17. The device of claim 16, where the light guiding material is a layer proximate to one of the scintillator, a radiographic imaging array or a substrate of the imaging array.

18. The device of claim 16, where the imaging array includes a substrate to support the imaging array and the scintillator includes a backing layer, where the substrate or the backing layer comprises a light guiding material.

* * * * *